(12) United States Patent
Kelly et al.

(10) Patent No.: US 7,579,317 B2
(45) Date of Patent: Aug. 25, 2009

(54) NUTRACEUTICAL COMPOSITION COMPRISING SOLUBLE KERATIN OR DERIVATIVE THEREOF

(75) Inventors: Robert J. Kelly, Christchurch (NZ); Gregory D. Ellis, Christchurch (NZ); Rebecca J. Macdonald, Christchurch (NZ); Robert A. McPherson, Lowood (AU); Paul G. Middlewood, Christchurch (NZ); Mark G. Nuthall, Christchurch (NZ); Guang-Feng Rao, Christchurch (NZ); Alisa D. Roddick-Lanzilotta, Lincoln (NZ); Gudmundur F. Sigurjonsson, Auckland (NZ); Diane J. Singleton, Christchurch (NZ)

(73) Assignee: Keratec, Ltd., Christchurch (NZ)

( * ) Notice: Subject to any disclaimer, the term of this patent is extended or adjusted under 35 U.S.C. 154(b) by 0 days.

(21) Appl. No.: 11/370,063

(22) Filed: Mar. 8, 2006

(65) Prior Publication Data

US 2007/0065506 A1 Mar. 22, 2007

Related U.S. Application Data

(60) Provisional application No. 60/660,458, filed on Mar. 11, 2005.

(51) Int. Cl.
*A61K 38/17* (2006.01)
*C07K 14/435* (2006.01)
(52) U.S. Cl. .................... 514/12; 530/357
(58) Field of Classification Search .......... 514/12; 530/357
See application file for complete search history.

(56) References Cited

U.S. PATENT DOCUMENTS

| | | | |
|---|---|---|---|
| 2,591,945 A | 4/1952 | Koerner et al. | |
| 3,567,363 A | 3/1971 | Wolfram | |
| 3,619,116 A | 11/1971 | Saville | |
| 3,644,084 A | 2/1972 | Hsiung et al. | |
| 3,883,647 A | 5/1975 | Geller | |
| 4,135,942 A | 1/1979 | Kikkawa | |
| 4,172,073 A * | 10/1979 | Kadri et al. | 530/357 |
| 4,407,793 A | 10/1983 | Akimora et al. | |
| 4,775,620 A * | 10/1988 | Cardiff et al. | 435/7.23 |
| 4,895,722 A | 1/1990 | Abe et al. | |
| 4,904,602 A | 2/1990 | Pigiet et al. | |
| 4,948,876 A | 8/1990 | Bore et al. | |
| 4,969,880 A | 11/1990 | Zamierowski | |
| 5,071,441 A | 12/1991 | Schnetzinger et al. | |
| 5,154,916 A | 10/1992 | Arraudeau et al. | |
| 5,358,935 A | 10/1994 | Smith et al. | |
| 5,460,967 A | 10/1995 | Fink | |
| 5,602,094 A * | 2/1997 | Goddard | 514/12 |
| 5,763,583 A | 6/1998 | Arai et al. | |
| 5,830,481 A | 11/1998 | Cauwet-Martin et al. | |
| 5,932,552 A | 8/1999 | Blanchard et al. | |
| 5,972,385 A | 10/1999 | Liu et al. | |
| 6,039,962 A | 3/2000 | Cauwet-Martin et al. | |
| 6,110,487 A | 8/2000 | Timmons et al. | |
| 6,124,265 A | 9/2000 | Timmons et al. | |
| 6,159,495 A | 12/2000 | Timmons et al. | |
| 6,203,574 B1 | 3/2001 | Kawamura | |
| 6,312,674 B1 | 11/2001 | Maubru et al. | |
| 6,432,435 B1 | 8/2002 | Timmons et al. | |
| 6,514,744 B2 | 2/2003 | Murata et al. | |
| 6,544,548 B1 | 4/2003 | Siller-Jackson | |
| 6,783,546 B2 * | 8/2004 | Zucherman et al. | 623/17.16 |
| 6,846,940 B2 | 1/2005 | Gaetani et al. | |
| 7,169,896 B2 * | 1/2007 | Schrooyen et al. | 530/350 |
| 2001/0018614 A1 | 8/2001 | Bianchi | |
| 2002/0004068 A1 | 1/2002 | DiDrusco | |
| 2002/0013408 A1 | 1/2002 | Rhee | |
| 2002/0035046 A1 | 3/2002 | Lukenbach et al. | |
| 2002/0183858 A1 | 12/2002 | Contiliano et al. | |
| 2003/0035820 A1 | 2/2003 | Timmons et al. | |
| 2003/0039676 A1 | 2/2003 | Boyce et al. | |
| 2006/0165635 A1 | 7/2006 | Kelly et al. | |
| 2006/0205652 A1 | 9/2006 | Zamora et al. | |

FOREIGN PATENT DOCUMENTS

| | | |
|---|---|---|
| CN | 1403643 | 3/2003 |
| CN | 1425813 | 6/2003 |
| EP | 0 628 573 A1 | 12/1994 |
| EP | 1 201 736 B1 | 4/2005 |
| FR | 1503640 | 12/1967 |
| FR | 2687577 A1 | 8/1993 |

(Continued)

OTHER PUBLICATIONS

Thomas et al., "In vitro reconstitution of wool intermediate filaments," Int J Biol Macromol 8;258-264, 1986.*
MacLaren, John A., et al., "Wool Science The Chemical Reactivity of the Wool Fibre", pp. 12-14, 1981.
Hunter, Emma A.L., et al., "Cysteine and Methionin Supplementation Modulate the Effect of Tumor Necrosis Factor a on Protein Synthesis, Glutathione and Zinc Concentration of Liver and Lung in Rats Fed a Low Protein Diet", American Institute of Nutrition, vol. 124, No. 12, pp. 2319-2328, 1994.
Homandberg, G.A., et al., "Fibronectin Fragment Mediated Cartilage Chondrolysis. I. Suppression by Anti-Oxidants", Biochemica et Biophysica Acta, vol. 1317, pp. 134-142, 1996.
Parcell, Stephen, "Sulphur in Human Nutrition and Applications in Medicine", Alternative Medicine Review, vol. 7, No. 1, pp. 22-44, 2002.

(Continued)

*Primary Examiner*—Delia M. Ramirez
*Assistant Examiner*—Rosanne Kosson
(74) *Attorney, Agent, or Firm*—Holland & Hart, LLP (57) ABSTRACT

Keratin and derivatives thereof, preferably S-sulfonated keratin intermediate filament protein, S-sulfonated keratin high sulfur protein, and S-sulfonated peptides provide antioxidant activity, e.g., that equal to 200-2200 μmol TEAC/100 g or 100 ml, and are useful in an oral supplement to cause reduction in oxidative stress and benefits stemming therefrom, e.g., promoting skin health and to provide anti-inflammatory effect.

11 Claims, 4 Drawing Sheets

FOREIGN PATENT DOCUMENTS

| | | |
|---|---|---|
| GB | 2 115 427 | 9/1983 |
| JP | 53-119900 | 10/1978 |
| JP | 54 137064 | 10/1979 |
| JP | 63-301809 | 12/1988 |
| JP | 03-007596 | 1/1991 |
| JP | 03-294297 | 12/1991 |
| JP | 05-222100 | 8/1993 |
| JP | 05-320358 | 12/1993 |
| JP | 06-100600 | 4/1994 |
| JP | 06-220713 | 8/1994 |
| JP | 06 192433 | 12/1994 |
| WO | WO 92/02238 | 2/1992 |
| WO | WO 98/51265 | 11/1998 |
| WO | WO 99/18922 | 4/1999 |
| WO | WO 99/19005 | 4/1999 |
| WO | WO 99/26570 | 6/1999 |
| WO | WO 00/23039 | 4/2000 |
| WO | WO 00/41739 | 7/2000 |
| WO | WO 00/70049 | 11/2000 |
| WO | WO 02/09659 | 2/2002 |
| WO | WO 03/011894 | 2/2003 |
| WO | WO 03/018673 | 3/2003 |
| WO | WO 03/103737 | 12/2003 |

OTHER PUBLICATIONS

Zafarullah, M., et al., "Molecular Mechanisms of N-Acetylcysteine Actions", Cellular and Molecular Life Sciences, vol. 60, No. 1, pp. 6-20, 2003.

Hummel, Klaus M., et al., "Cysteine Proteinase Cathepsin K mRNA is Expressed in Synovium of Patients with Rheumatoid Arthritis and Is Detected at Sites of Synovial Bone Destruction", Journal of Rheumatology, vol. 25, No. 10, pp. 1887-1984, 1998.

Bradley, Helen, et al., "Sulfate Metabolism is Abnormal in Patients with Rheumatoid Arthiritis", Journal of Rheumatology, vol. 21, No. 7, pp. 1192-1196, 1994.

Wilkinson, L.J., et al., "Cysteine Diosygenase: Modulation of Expression in Human Cell Lines by Cytokines and Control of Sulphate Production", Toxicology in Vitro, vol. 16, pp. 481-483, 2002.

Tappaz, M.L., "Taurine Biosynthetic Enzymes and Taurine Transporter: Molecular Identification and Regulations", Neurochemical Research, vol. 29, No. 1, pp. 83-96, Jan. 2004.

Kontny, E., et al., "Impaired Generation of Taurine Chloramine by Synovial Fluid Neutrophils of Rheumatoid Arthritis Patients", Amino Acids, vol. 24, No. 4, pp. 415-418, 2002.

Roughley, Peter J., et al., "Cartilage Proteoglycans: Structure and Potential Functions", Microscopy Research and Technique, vol. 28, No. 5, pp. 385-397, 1994.

Rossi, Antonio, et al., "In Vitro Proteoglycan Sulfation Derived from Sulfhydryl Compounds in Sulfate Transporter Chondrodysplasias", Pediatric Pathology and Molecular Medicine, vol. 22, No. 4, pp. 311-321, 2003.

Kusche-Gullberg, Marion, et al., "Sulfotransferases in Glycosaminoglycan Biosynthesis", Current Opinion in Structural Biology, vol. 13, pp. 605-611, 2003.

Rath, Virginia L., "Sulfotransferase Structural Biology and Inhibitor Discovery", Drug Discovery Today, vol. 9, No. 23, pp. 1003-1011, Dec. 2004.

Venkatachalam, K.V., "Human 3'-phosphoadenosine 5'-phosphosulfate (PAPS) Synthase: Biochemistry, Molecular Biology and Genetic Deficiency", IUBMB Life, vol. 55, pp. 1-11, 2003.

Heyland, Daren K., et al., "Antioxidant Nutrients: A Systematic Review of Trace Elements and Vitamins in the Critically Ill Patient", Intensive Care Med., vol. 31, pp. 327-337, 2005.

Elsayed, Nabil M., "Antioxidant Mobilization in Response to Oxidative Stress: A Dynamic Environmental-Nutritional Interaction", Nutrition, vol. 17, pp. 828-834, 2001.

Serhan, Charles N., et al., "Resolution of Inflammation: The Beginning Programs the End", Nature Immunology, vol. 6, No. 12, pp. 1191-1197, Dec. 2005.

Henson, Peter M., "Dampening Inflammation", Nature Immunology, vol. 12, No. 12, pp. 1179-1182, Dec. 2005.

Verbruggen, G., "Chondroprotective Drugs in Degenerative Joint Diseases", Journal of Rheumatology, vol. 45, pp. 129-138, 2006.

Largo, R., et al., "Glucosomine Inhibits IL-1b-Induced NFkB Activation in Human Osteoarthritic Chondrocytes", OsteoArthritis and Cartilage, vol. 11, pp. 290-298, 2003.

Chan, P.S., et al., "Glucosamine and Chondroitin Sulfate Regulate Gene Expression and Synthesis of Nitric Oxide and Prostaglandin E2 in Articular Cartilage Explants", OsteArthritis and Cartilage, vol. 13, pp. 387-394, 2005.

Rassin, D.K., et al., "Nutritional Approaches to Improve Cognitive Development During Infancy: Antioxidant Compounds", Acta Paediatr Suppl., vol. 442, pp. 34-41, 2003.

Brugge, Karen L., et al., "The Role of Alterations in Free Radical Metabolism in Mediating Cognitive Impairments in Down's Syndrome", EXS, vol. 62, pp. 190-198, 1992.

Del Marmol, Veronique, et al., "Cysteine Deprivation Promotes Eumelanogenesis in Human Melanoma Cells", Journal of Investigative Dermatology, vol. 107, No. 5, pp. 698-702, 1996.

Smit, Nico P.M., et al., "Melanogenesis in Cultured Melanocytes Can Be Substantially Influenced by L-Tyrosine and L-Cysteine", Journal of Investigative Dermatology, vol. 109, No. 6, pp. 796-800, 1997.

Fujiwara, Y., et al., "Effect of Simultaneous Administration of Vitamin C, L-Cysteine and Vitamin E on the Melanogenesis", Biofactors, vol. 21, Nos. 104, pp. 415-418, 2004.

Kong, Kwang-Hoon, et al., "Expression and Characterization of Human Tyrosinase From a Bacterial Expression System", Comparative Biochemistry and Physiology, Part B, vol. 125, pp. 563-569, 2000.

Yamamura, Tatsuo, et al., "Antimelanogenic Activity of Hydrocoumarins in Cultured Normal Human Melanocytes by Stimulating Intracellular Glutathione Synthesis", Archives of Dermatological Research, vol. 294, No. 8, pp. 349-354m 2002.

Alonso, Laura C., et al., "Molecular Genetic and Endocrine Mechanisms of Hair Growth", Hormone Research, vol. 60, pp. 1-13, 2003.

Olney, J.W., et al., Brain Damage in Infant Mice Following Oral Intake of Glutamate, Aspartate or Cysteine, Nature, vol. 227, pp. 609-610, 1970.

Riise, G.C., "The Intrabronchial Microbial Flora in Chronic Bronchitis Patients: A Target for N-Acetylcysteine Therapy", European Respiratory Journal, vol. 7, pp. 94-101, 1994.

Grandjean, E.M., et al., "Efficacy of Oral Long-Term N-Acetylcysteine in Chronic Bronchopulmonary Disease: A Meta-Analysis of Published Double-Bline, Placebo-Controlled Clinical Trials", Clinical Therapy, vol. 22, pp. 209-221, 2000.

Hansen, N.C.G., et al., Orally Administered N-Acetylcysteine May Improve General Well-Being in Patients with Mild Chronic Bronchitis, Respitory Medicine, vol. 88, pp. 531-535, 1994.

Rasmussen, J.B., et al., Reduction in Days of Illness After Long-Term Treatment with N-Acetylcysteine Controlled-Release Tablets in Patients with Chronic Bronchitis, European Respitory Journal, vol. 1, pp. 351-355, 1988.

Parr, G.D., et al., Oral Fabrol (oral N-acetylcysteine) in Chronic Bronchitis, British Journal of Diseases of Chest, vol. 81, pp. 341-348, 1987.

Ardissino, D., et al., "Effect of Transdermal Nitroglycerin or N-acetylcysteine, or Both, in the Long-Term Treatment of Unstable Angina Petoris", Journal of the American College of Caridiology, vol. 29, pp. 941-947, 1997.

Estensen, R.D., et al., "N-acetylcysteine Suppression of the Proliferative Index in the Colon of Patients with Previous Adenomatous Colonic Polyps", Cancer Letters, vol. 147, pp. 109-114, 1999.

Kinscherf, R., et al., Effect of glutathione Depletion and Oral N-acetylcysteine Treatment on CD4+ and CD8+ Cells. FASEB Journal, vol. 8, pp. 448-451, 1994.

Akerlund, et al., "Effect of N-acetylcystine (NAC) Treatment on HIV-1 Infections: A Double-Blind Placebo-Controlled Trial", European Journal of Clinical Pharmacology, vol. 50, pp. 457-461, 1996.

Zhang, Shumin, et al., "A Prospective Study of Plasma Total Cysteine and Risk of Breast Cancer", Epidemiology Biomarkers & Prevention, vol. 12, pp. 1188-1193, 2003.

James, L.P., et al., "Effect of N-Acetylcysteine on Acetaminophen Toxicity in Mice: Relationship to Reactive Nitrogen and Cytokine Formation", Toxicological Sciences, vol. 75, No. 2, pp. 458-467, 2003.

Shankar, K., et al., "Type 1 Diabetic Mice are Protected fro mAcetaminophen Hepatotoxicity", Toxicology Sciences, vol. 72, No. 2, pp. 220-234, 2003.

Goodman, M.T., Case-Control Study of Plasma Folate, Homocysteine, Vitamin B12, and Cysteine as Markers of Cervical Dysplasia, Cancer, vol. 89, No. 2, pp. 376-382, 2000.

Bernard, G.L. et al., "A Trial of Antioxidants N-Acetyclysteine and Procysteine in ARDS. The Antioxidant in ARDS Study Group", Chest, vol. 112, pp. 164-172, 1997.

Tepel, M., et al., "Prevention of Radiographic-Contrast-Agent-Induced Reductions in Renal Function by Acetylcysteine", New England Journal of Medicine, vol. 343, pp. 180-184, 2000.

Walters, M.T., et al., "A Double-Blind, Cross-Over, Study of Oral N-Acetylcysteine in Sjogren's Syndrome", Scand J. Rheumatol Suppl., vol. 61, pp. 253-258, 1986.

De Vries, N., et al., "N-acetyl-l-cysteine", Journal of Cellular Biochemistry Supplement, vol. 17F, pp. 270-277, 1993.

Beloqui, O., et al., "N-aceytl Cysteine Enhances the Response to Interferon-Alpha in Chronic Hepatitis C: A Pilot Study", Journal of Interferon Research, vol. 13, pp. 279-282, 1993.

Feghali, J.G., et al., "L-n-acetyl-cysteine Protection Against Cisplatin-Induced Auditory Neuronal and Hair Cell Toxicity", Laryngoscope, vol. 111, No. 7, pp. 1147-1155, 2001.

Balli, R., "Controlled Trial on the Use of Oral Acetylcysteine in the Treatment of Glue-Ear Following Drainage", European Journal of Respitory Diseases, vol. 61, Suppl. 111, pp. 159, 1980.

Yalcin, E. et al., "N-acetylcysteine in Chronic Blepharitis", Cornea, vol. 21, pp. 164-168, 2002.

De Flora, S., et al., "Mechanisms fo N-acetylcysteine in the Prevention of DNA Damage and Cancer, with Special Reference to Smoking-Related End-Points", Carcinogenesis, vol. 22, pp. 999-1013, 2001.

Connors, S.L., et al., "Secretin and Autism: The Role of Cysteine", Journal of the American Academy of Child and Adolescent Psychiatry, vol. 38, pp. 795-796, 1999.

Apple, S.K., et al., "Effect of Feather Meal on Live Animal Performance and Carcass Quality and Composition of Growing Finishign Swing", Journal of Animal Science, vol. 81, pp. 172-181, 2003.

Loy, T.W., et al., "Effects of Supplementation on Intake an Growth of Nursing Calves Grazing Native Range in Southeastern North Dakota", Journal of Animal Science, vol. 80, pp. 2717-2725, 2002.

Pohl, Thomas, "Concentration of Proteins and Removal of Solutes", Methods in Enzymology, vol. 182, pp. 68-83, 1990.

McNeil, Steven, "Heavy Metal Removal Using Wool Filters", Asian Textile Journal, pp. 88-90, May-Jun. 2001.

Fukatsu, K., "Degradation of Fe(III)—Wool Keratin Complex by Hydrogen Peroxide", Kumanoto Women's University, Kumamoto, Japan, Sen'i Gakkaishi (Fiber), vol. 46, No. 5. pp. 186-191 1990.

Thomas, Helga, et al., "In Vitro Reconstitution of Wool Intermediate Filaments", Int. J. Biol. Macromol., vol. 8, pp. 258-264, Oct. 1986.

Harrap, B.S., et al., "Soluble Derivatives of Feather Keratin", Biochem J., vol. 92, No. 8, pp. 8-18, 1964.

Swan, J.M., "The Reaction of Protein Thiol and Disulphide Groups with Cupric Sulphite Solutions", pp. 69-83, Sep. 1960.

Mies, Von H.H., et al., "Praparative Gewinnung loslicher Proteine Aus Wolle", Das Leder, pp. 1-9, Jan. 1988.

Thomas, Helga, et al., "Experiments for the Isolation of Matrix Proteins of Wool in Disulphide Form", Melliand Textilberichte, pp. 297-300, Apr. 1983.

Goto M, Suyama K, "Occlusion of Transition Metal Ions by New Adsorbents Synthesized from Plant Polyphenois and Animal Fibrous Proteins", www.pubmed.gov, Dec. 18, 2006.

Mies, H.H., et al., "Chromatographic and Electrophoretic Investigation of the Properties of Unprotected Low-Sulphur Wool Kerateins", Journal of Chromatography, vol. 405,. p. 365-370, 1987.

Pavlath, Attila E., et al., "Clarity of Films from Wool Keratin", Textile Res. J., vol. 69, No. 7, pp. 539-541, 1999.

Platt, A.J., et al., "A Comparative Study of Silicone Net Dressing and Paraffin Gauze Dressing in Skin-Grafted Sites", Burns, vol. 22, No. 7, pp. 543-545, 1996.

Valenta, Claudia, et al., "The Use of Polymers for Dermal and Transdermal Delivery", European Journal of Pharmaceutics and Biopharmaceutics, vol. 58, pp. 279-289, 2004.

Jonkman, Marcel F., et al., "New Method to Assess the Water Vapour Permeance of Wound Coverings", Biomaterials, vol. 9, pp. 263-267, May 1988.

Ming Yang, Jen, et al., "Properties of Chitosan Containing PP-g-AA-g-NIPAAm Bigraft Nonwoven Fabric for Wound Dressing", Journal of Membrane Science, vol. 243, pp. 1-7, 2004.

Freedman, Gordon, et al., "Practical Treatment of Pain in Patients with Chronic Wounds: Pathogenesis-Guided Management", The American Journal of Surgery, vol. 188, pp. 31S-35S, 2004.

Coderch, L., et al., "Chromatographic Characterization of Internal Polar Lipids from Wool", JAOCS, vol. 72, No. 6, pp. 715-720, 1995.

Coderch, L., et al., "Physicochemical Characteristics of Liposomes Formed with Internal Wool Lipids", JAOCS, vol. 73, No. 12, pp. 1713-1718, 1996.

Wertz, Philip W., et al., "The Composition of the Ceremides from Human Stratum Corneum and from Comedones", The Journal of Investigative Dermatology, vol. 84, No. 5, pp. 410-412, 1985.

Matsumoto, Kiyoichi, et al., "Studies on Regenerated Protein Fibers, III. Production of Regenerated Silk Fibroin Fiber by the Self-Dialyzing West Spinning Method", Journal of Applied Polymer Science, vol. 60, pp. 503-511, 1996.

Yang, Yiqi, et al., "Formaldehyde-Free Zein Fiber-Preparation and Investigation", Journal of Applied Polymer Science, vol. 59, pp. 433-441, 1996.

Cates, David M., et al., "Preparation and Properties of Fibers Containing Mixed Polymers III. Polyacrylonitrile-Silk Fibers", Journal of Polymer Science, vol. 21, No. 97, pp. 125-138, 1956.

Schimpf, Warren C., "Fibers from Regenerated Collagen", Ind. Eng. Chem., Prod. Res. Dev., vol. 16, No. 1, pp. 90-92, 1977.

Sastry, T.P., et al., "Graft Copolymerization of Feather Keratin Hydrolyzate: Preparation and Characterization", Journal of Polymer Materials, vol. 14, No. 2, pp. 177-181, 1997.

Tanabe, Toshizumi, et al., "Preparation and Characterization of Keratin-Chitosan Composition Film", Biomaterials, vol. 23, pp. 817-825, 2002.

Marshall, R.C., et al., "Structure and Biochemistry of Mammalian Hard Keratin", Electron Microsc. Rev., vol. 4, pp. 47-83, 1991. Journal of Applied Polymer Science, vol. 91, pp. 756-762, 2004.

Gillespie, J.M., et al., "Variability in the Proteins of Wool and Hair", Division of Protein Chemistry, CSIRO, vol. 2, pp. 67-77, 1980.

Milgram, Norton W., et al., "Landmark Discrimination Learning in the Dog: Effects of Age, an Antioxidant Fortified Food, and Cognitive Strategy", Neuroscience and Biobehavioral Reviews, vol. 26, pp. 679-695, 2002.

Kazunori, Katoh, et al., "Preparation and Properties of Keratin-Poly(vinyl alchohol) Blend Fiber", Journal of Applied Polymer Science, vol. 91, pp. 756-762, 2004.

Yamauchi, Kiyoshi, et al., "Cultivation of Fibroblast Cells on Keratin-Coated Substrata", J. Biomater Sci. Polymer Edn., vol. 9, No. 3, pp. 259-270, 1998.

Braverman, E.R., et al., "The Healing Nutrients Within: Facts, Findings, and New Research on Amino Acids", Basic Health Publications, Inc. 2003.

Gillespie, J. Morton, "The Structural Proteins of Hair: Isolation, Characterization, and Regulation of Biosynthesis", Biochemistry and Physiology of the Skin, pp. 475-510, 1983.

* cited by examiner

NUTRACEUTICAL COMPOSITION COMPRISING SOLUBLE KERATIN OR DERIVATIVE THEREOF

CROSS-REFERENCE TO RELATED APPLICATIONS

This application claims benefit of U.S. Provisional Application No. 60/660,458, filed Mar. 11, 2005.

TECHNICAL FIELD

This invention is directed to keratin and water soluble keratin fractions and peptides and derivatives thereof in an oral supplement, i.e., in a nutraceutical, and/or for prophylaxis or treatment of a wide range of health conditions.

BACKGROUND OF THE INVENTION

Reactive oxygen species (ROS), such as hydrogen peroxide, the superoxide and hydroxyl radicals, are well recognized as having a damaging effect to biological tissue and biochemical pathways at a cellular level. An imbalance between oxidants and antioxidants within a cell can create a situation of oxidative stress, resulting in an increase in ROS levels and a variety of negative health consequences.

Specifically in relation to joint health ROS have been implicated in the ageing in cartilage and osteoarthritis. Mechanisms of degradation include ROS acting as signaling mediators in the tumor necrosis factor alpha stimulus of inflammatory arthritis.

Sulphur rich species, such as glutathione, cysteine and thioredoxin are crucial parts of the cells own protection mechanism. Sulfhydryl groups are vital in maintaining the oxidant anti oxidant balance within a cell and preventing situations of oxidative stress. For example, patients with rheumatoid arthritis are known to be deficient of cellular glutathione, and have a subsequent oxidant anti oxidant imbalance.

Synthetic compounds, such as N-acetylcyseine have been shown to protect against damage from ROS. A range of sulphur rich species, including amino acids and derivatives, such as glutathione, cysteine, homocysteine, methionine, N-acetyl cysteine have been used to combat oxidative stress. The effectiveness of these species at influencing the body's ability to combat oxidative stress is variable, with glutathione for example having limited bioavailability when ingested as an oral supplement.

The need exists for natural derived materials and derivatives thereof that improve the bodies ability to respond to oxidative stress. The provision of natural sources of important sulphur rich amino acids as an oral supplement is of particular value.

SUMMARY OF THE INVENTION

The invention herein in one embodiment, denoted the first embodiment, is directed to composition comprising keratin ingredient, e.g., keratin, water soluble keratin fraction, water soluble keratin peptide, and/or derivative thereof, as an oral supplement and nutraceutical for affecting redox pathways, for antioxidant effect, to reduce oxidative stress and for the prophylaxis or improvement of a wide range of health conditions, including those caused by or associated with oxidative stress, e.g., in respiratory disorders (to help dissolve mucus, loosen phlegm and improve symptoms associated with chronic bronchitis, asthma, cystic fibrosis and emphysema and reduce the number of attacks of acute bronchitis in smokers and to increase lung surfactants to ameliorate symptoms of acute respiratory distress syndrome), to reduce incidence of heart attacks and other severe heart problems when combined with nitroglycerin administration, for inhibiting formation of malignant cells in colon cancer, to enhance immune function in AIDS/HIV, to reduce risk of breast cancer, to prevent or reduce liver and kidney damage associated with overdose of acetaminophen, to decrease risk of cervical dysplasia, to protect kidneys from contrast agents administered in the course of x-ray diagnosis, for treating Sjogren's syndrome, to provide protective effects for oral, laryngeal or lung cancer, to prevent or reduce resistance to interferon alpha in the treatment of hepatitis C infection, to protect against hearing loss from noise, ototoxic drugs and ageing, to prophylax against abnormality of tear film in blepharitis, to help neutralize heavy metal toxins and toxic by-products of smoking, smog, alcohol and fats, to stabilize secretin preparation for administration to autistic children, for joint health and for antioxidant effect, for anti-inflammatory effect, for promoting skin health (by promoting skin cell proliferation; by promoting increased antioxidant effect thereby protecting against damage from free radicals, e.g., sun damage; by potentiating the formation and maintenance of a moisture barrier just below the outer surface of the skin to cause moisture to be retained in the body, thereby preventing dehydration (drying out) of the skin; by promoting wound healing; and by promoting skin tone and radiance), to promote cognitive abilities, such as those promoted by glutathione and antioxidants, to prevent chronic inflammation, for example chronic joint or other inflammation mediated by interleukins and prostaglandins, to promote hair growth, and for total body health.

The term "keratin ingredient" is used herein to include keratin, water soluble keratin fraction, water soluble keratin peptide and/or derivative thereof.

The invention herein in a second embodiment is directed to keratin ingredient, e.g., keratin, water soluble keratin fraction, water soluble keratin peptide, and/or derivative thereof, for use in human or veterinary medicine.

The invention herein in a third embodiment is directed to use of keratin ingredient, e.g., keratin, water soluble keratin fraction, water soluble keratin peptide, and/or derivative thereof, for the prophylaxis or treatment of disorders caused by or associated with oxidative stress.

The invention herein in a fourth embodiment is directed to use of a keratin ingredient, e.g., keratin, water soluble keratin fraction, water soluble keratin peptide, and/or derivative thereof, to provide anti-inflammatory effect, e.g., for joint health, e.g., for the prophylaxis or treatment of degenerative joint disease.

The invention herein in a fifth embodiment is directed to use of a keratin ingredient, e.g., keratin, water soluble keratin fraction, water soluble keratin peptide, and/or derivative thereof, to promote skin health.

The invention herein in a sixth embodiment is directed to preparing water soluble S-sulfonated keratin fraction and formulating it into an oral supplement composition or a nutraceutical composition.

DETAILED DESCRIPTION

As indicated above, the compositions herein can comprise keratin ingredient, e.g., keratin, water soluble keratin fraction, water-soluble keratin peptide, and/or derivatives thereof.

The water soluble keratin fractions have molecular weight ranging from 0.5 to 60 kDa. They include intact proteins and hydrolyzed proteins (peptides). They include intermediate filament protein (IFP), ultra high sulfur protein (UHSP), high sulfur protein (HSP), high glycine high tyrosine protein (HGTP). Derivatives of these for use in the invention herein include the above where S—S is converted to S—$SO_3^-$ (S-sulfonated) by oxidative sulfitolysis, where S—S is converted to $SO_3^-$ (sulfonic acid groups) by partial oxidation, and where S—S is converted to cysteic acid groups by partial oxidation, e.g., the partial oxidation being carried out, for example, with hydrogen peroxide, peracetic acid, perborate, percarbonate, benzoyl peroxide, or ammonium sulfate peroxide.

Excluded from the derivatives of soluble keratin fractions herein are keratin peptides with residual SH from reduction of S—S in amounts of 10% or more.

The hard alpha keratin proteins such as those derived from human hair, wool, animal fibres, horns, hooves or other animal sources, can be classified into particular components according to their biochemical properties, specifically their molecular weight and amino acid composition.

Table 1 below illustrates the amino acid composition determined by conventional analytical methods of typical keratin protein fractions known in the art and also the subject of this invention. This involves acid hydrolysis of the analyte which converts all cystine and labile cysteine derivatives to cysteine, typically recorded as half-cystine.

TABLE 1

| | SIFP and SIFP-Pep | SHSP and SHSP-Pep | SPEP | IFP | HSP | HGTP | Whole Wool |
|---|---|---|---|---|---|---|---|
| Cya | 0.4 | 1.7 | 0.7 | 0 | 0 | 0 | 0 |
| Asp | 7.9 | 2.6 | 8 | 9.6 | 2.3 | 3.3 | 5.9 |
| Glu | 15.4 | 8.6 | 15 | 16.9 | 7.9 | 0.6 | 11.1 |
| Ser | 10.9 | 14.3 | 11.4 | 8.1 | 13.2 | 11.8 | 10.8 |
| Gly | 8.1 | 9.1 | 8.4 | 5.2 | 6.2 | 27.6 | 8.6 |
| His | 0.9 | 0.8 | 0.9 | 0.6 | 0.7 | 1.1 | 0.8 |
| Arg | 7.9 | 6.8 | 6.9 | 7.9 | 6.2 | 5.4 | 6.2 |

TABLE 1-continued

| | SIFP and SIFP-Pep | SHSP and SHSP-Pep | SPEP | IFP | HSP | HGTP | Whole Wool |
|---|---|---|---|---|---|---|---|
| Thr | 6.5 | 10.4 | 6.5 | 4.8 | 10.2 | 3.3 | 6.5 |
| Ala | 7.5 | 3.6 | 7.5 | 7.7 | 2.9 | 1.5 | 5.2 |
| Pro | 5.4 | 12.6 | 5.7 | 3.3 | 12.6 | 5.3 | 6.6 |
| Tyr | 1.1 | 1.8 | 1.2 | 2.7 | 2.1 | 15.0 | 3.8 |
| Val | 6.5 | 6.3 | 5.8 | 6.4 | 5.3 | 2.1 | 5.7 |
| Met | 0.2 | 0 | 0.3 | 0.6 | 0 | 0 | 0.5 |
| Lan | 0.2 | 0.2 | 0.3 | 0 | 0 | 0 | 0 |
| Ile | 3.7 | 2.9 | 3.4 | 3.8 | 2.6 | 0.2 | 3 |
| Leu | 8.9 | 3.9 | 8 | 10.2 | 3.4 | 5.5 | 7.2 |
| Phe | 2.5 | 1.5 | 2.1 | 2 | 1.6 | 10.3 | 2.5 |
| Lys | 2.1 | 0.4 | 2.1 | 4.1 | 0.6 | 0.4 | 2.7 |
| Cys | 4.2 | 12.4 | 4.6 | 6 | 22.1 | 6.0 | 13.1 |

Table 1 illustrates an amino acid composition of keratin fractions: S-sulfonated keratin intermediate filament protein (SIFP), peptides derived from S-sulfonated keratin intermediate protein (SIFP-pep), S-sulfonated keratin high sulfur protein (SHSP), peptides derived from S-sulfonated keratin high sulfur protein (SHSP-pep), S-sulfonated keratin peptide (SPEP) as used in the invention. Data on intermediate filament protein (IFP), high sulfur protein (HSP), high glycine-tyrosine protein (HGTP) and whole wool are courtesy of Gillespie and Marshall, *Variability in the proteins of wool and hair*, Proc. Sixth Int. Wool Text. Res. Conf., Pretoria, 2, 67-77, 1980. All residues are expressed as mol %. S-sulfocysteine, cystine and cysteine are measured as S-carboxymethyl cysteine following reduction and alkylation, and reported as cys.

Table 2 illustrates the molecular weight of the keratin fractions listed above as well as for S-sulfonated ultra high sulfur protein (SUHSP), S-sulfonated high glysine-tyrosene protein (SHGTP) and keratin peptides (PEP).

TABLE 2

| SIFP | 40-60 kD |
|---|---|
| SUHSP | 25-40 kD |
| SHSP | 10-30 kD |
| SHGTP | 5-15 kD |
| SPEP, SIFP-pep, SHSP-pep | 0.5-4 kD |
| IFP | 40-0 kD |
| UHSP | 25-40 kD |
| HSP | 10-30 kD |
| HGTP | 5-15 kD |
| PEP, IFP-pep, HSP-pep | 0.5-4 kD |

Table 2 illustrates the molecular weight determined by conventional analytical methods of typical keratin protein fractions known in the art and also the subject of this invention. Conventional analysis involves cleavage of cystine bonds within the keratin using reduction so that the protein mass is determined in its native, uncrosslinked state, most similar to the unkeratinised state of the protein. Mass is determined using mass spectrometry. Using these methods the keratin is made soluble without any hydrolysis of peptide bonds and an accurate measure of molecular weight is determined.

Both amino acid composition and molecular weight varies across keratin types, between species and also within breeds of one species, for example between wools from different breeds of sheep. The figures given in Tables 1 and 2 are indicative for the keratin source stated. However, individual types of keratin proteins, or keratin protein fractions, have distinctive characteristics, particularly molecular weight and amino acid content.

UHSP and HGTP proteins are described in Maclaren, J. A., et al., *Wool Science: The Chemical Reactivity of the Wool Fibre*, Science Press, Australia, ISBN 085583 107(3), 1981 and Marshall, R. C., "*Structure and Biochemistry of Mammalian Hard Keratin*," Electron Microscopy 4, 47, 1991, the whole of which are incorporated herein by reference. UHSP can contain 20-34 mol % cystine.

Keratin peptides (PEP) are formed by treating keratin source with strong acid or strong base or proteolytic enzyme to break the peptide bonds of the protein.

In one case herein the water soluble keratin fractions and derivatives thereof have molecular weight greater than 10 kDa.

In one case herein, the water soluble protein fractions and derivatives thereof are S-sulfonated derivatives. The degree of S-sulfonation of SIFP and SHSP is 75-100% (i.e., cystine is S-sulfonated, e.g., 80-90%, with that not S-sulfonated being present as cysteic acid). The degree of sulfonation of SPEP is in the range of 65-100%, e.g., 65-85%. A preferred water soluble keratin fraction or derivative thereof for use herein is SIFP.

The SIFP used herein is an off white odorless powder passing through 300 μm mesh and containing 89-98% protein and is soluble above pH4.

A subject of the invention is formulations containing intact S-sulfonated keratin protein fractions. "Intact" refers to proteins that have not been significantly hydrolyzed, with hydrolysis being defined as the cleavage of bonds through the addition of water. Gillespie (*Biochemistry and physiology of the skin*, vol. 1, Ed. Goldsmith Oxford University Press, London, 1983, pp. 475-510) considers "intact" to refer to proteins in the keratinized polymeric state and further refers to polypeptide subunits which complex to form intact keratins in wool and hair. For the purpose of this invention "intact" includes the polypeptide subunits described by Gillespie. These are equivalent to the keratin proteins in their native form without the disulfide crosslinks formed through the process of keratinisation.

Keratin protein fractions are distinct groups from within the keratin protein family, such as the intermediate filament proteins, the high sulfur proteins or the high glycine-tyrosine proteins well known in the art. Intermediate filament proteins are described in detail by Orwin et al. (*Structure and Biochemistry of Mammalian Hard Keratin*, Electron Microscope Reviews, 4, 47, 1991) and also referred to as low sulphur proteins by Gillespie (*Biochemistry and physiology of the skin*, vol. 1, Ed. Goldsmith Oxford University Press, London, 1983, pp. 475-510). Key characteristics of this protein family are molecular weight in the range of 40-60 kD and a cysteine content (measured as half cystine) of around 4%. The high sulfur protein family are also well described by Orwin and Gillespie in the same publications. This protein family has a large degree of heterogeneity but can be characterized as having a molecular weight in the range 10-30 kD and a cysteine content of greater than 10%. A subset of this family, the ultra high sulfur proteins, can have a cysteine content of up to 34%. The high glycine-tyrosine protein family are also well described by Orwin and Gillespie in the same publications. This family is also referred to as the high tyrosine proteins and has characteristics of a molecular weight less than 10 kDa, a tyrosine content typically greater than 10% and a glycine content typically greater than 20%.

For the purpose of this invention a "keratin protein fraction" is a purified form of keratin that contains predominantly, although not entirely, one distinct protein group as described above. In the context of this invention S-sulfonated keratins have cysteine/cystine present predominantly in the form S-sulfocysteine, commonly known as the Bunte salt. This highly polar group imparts a degree of solubility to proteins. Whilst being stable in solution, the S-sulfo group is a labile cysteine derivative, highly reactive towards thiols, such as cysteine, and other reducing agents. Reaction with reducing agents leads to conversion of the S-sulfo cysteine group back to cysteine. S-sulfo cysteine is chemically different from cysteic acid, although both groups contain the $SO_3^-$ group. Cysteic acid is produced irreversibly by the oxidation of cysteine or cystine and once formed cannot form disulfide crosslinks back to cysteine. S-sulfocysteine is reactive towards cysteine and readily forms disulfide crosslinks.

Methods of preparation of S-sulfonated protein fractions SIFP, SHSP and SPEP are outlined in WO 03/011894 A1 which is incorporated herein by reference in its entirety. The keratin source can be, for example, animal wool, hair, horns, hooves, feathers or scales.

As indicated in WO 03/011894 A1, SIFP, SHSP and SPEP are prepared using digestion and extraction steps.

The preferred digestion procedure is that of Example 1a of WO 03/011894 A1 with the following differences. Instead of 8 liters of concentrated ammonia, 2.4 liters is used. The dilution with water is to 150 liters. Instead of 15 L of sulfuric acid, 4 L is used to take the pH down to 8.6. The temperature of digestion is raised from 20° C. to 25° C. The 24 hours of gentle agitation is reduced to 6 hours, liquor is sprayed through a spray ring over liquor surface to entrain air and assure enough oxygen present to catalyze the copper (I) to copper (II). When filtering, the digest liquor is not passed through a fresh wool filter but is still treated with the Purolite resin. After fresh water is added, air can be introduced to oxidize residual sulfite.

Preferably a combination of Examples 2a and 2b of WO 03/011894 A1 is used for the extraction step. The batch part of the method is used prior to continuous extraction. In the batch part of the method the step of agitating for 4 hours following homogenization is omitted. Air is introduced to oxidize the residual sulfite. Following the batch processing the continuous extraction of Example 2b is used but for 48-72 hours.

The process for obtaining SIFP is preferably that of Example 3c of WO 03/011894 A1, if other products are also desired, with the following differences: The pH is lowered using 2M sulfuric acid. The protein precipitate is isolated by a rack-off valve, screen, filter press or centrifuge and the isolated protein precipitate is then combined and washed for 2-20 hours in pH2 sulfuric acid (2M) to leach the copper into solution. Then the precipitate is redissolved with dilute sodium hydroxide and mixed with 0.2M EDTA at a rate of 160 ml/L. The protein is re-precipitated with 2M sulfuric acid and rinsed with water 2 or 3 times and dissolved with dilute sodium hydroxide and dried by freeze-drying, fluidized bed drying or spray drying, to obtain the SIFP.

The filtrate in said Example 3c following the initial pH induction step contains SUHSP, SHSP and SHGTP which are recovered by membrane filtration, e.g., ultrafiltration (UF) as in Example 3a or UF followed by nanofiltration (NF) or reverse osmosis (RO) on the UF permeate. SUHSP, SHSP and SHGTP do not have to be dried and can be used aqueously in a drink or such rather than as a water soluble powder.

If other products besides SIFP are not also desired the preferred process of obtaining SIFP may be Example 3a of WO 03/011894 A1.

The preferred method for isolating SPEP from the residual wool mass of Example 2 of WO 03/011894 A1 is Example 4c of WO 03/011894 A1 with the following differences: The pH is maintained at 9.5 and the reaction held at 40° C. for a minimum of 6 hours. The enzyme (activity of 580,000 DU/g)

is added at 1 mg/g of solid keratin residue. The pH is then lowered to 3.5 and the dilute peptide is filtered through a screen and then centrifuged. The centrate SPEP (i.e., from the centrifuge) is passed over ion exchange and concentrated using a scraped film evaporator, vacuum flash evaporator or reverse osmosis membrane depending on the final desired properties and color. It is possible to spray dry the concentrated SPEP stream.

We turn now to administration of the keratin ingredient, namely keratin, water soluble keratin fraction, water soluble keratin peptide and derivative thereof.

The delivery route is oral, e.g., in the form of a tablet, capsule, powder, fizzy table, drink, gel (for drinking), chewing gum, dissolvable strip, lozenge, sublingual table, soluble powder or liquid.

Examples of diluents/stabilizers for formulations of the keratin, water soluble keratin fraction, water soluble keratin peptide, and derivatives thereof, include cellulose and derivatives thereof, starches and derivatives thereof, and sugars and derivates thereof, including, for example, microcrystalline cellulose, cellulose, starch (potato, tapioca and rice), dextrose, lactose, maltodextrin, sugar and sugar alcohol (mannitol, soybitol, xylitol, etc.). Other diluents/stabilizers are, for example, calcium phosphate and magnesium stearate.

Synergistic ingredients used in formulation with the keratin, water soluble keratin fraction, water soluble keratin peptide and derivative thereof, include, for example, vitamins C,E,B; proteins (e.g., collagen), carbohydrates (e.g., hyaluronic acid, chondroitin sulfate, glucosamine), amino acids and peptides (e.g., glutathione, cystine, cysteine, homocysteine, methionine).

Oral supplement and/or nutraceutical compositions for all the embodiments herein are for example those comprising from 0.1 to 99.9%, e.g., 0.1 to 90%, e.g., 0.1 to 80%, e.g., 0.1 to 70%, e.g., 0.1 to 60%, by weight keratin ingredient selected from the group consisting of keratin, water soluble keratin fraction, water soluble keratin peptide, derivatives of these and mixtures thereof and at least one of from 40 to 90% by weight of cellulose and/or derivatives thereof, from 15 to 60% starch and/or derivative thereof, from 2 to 95% by weight of sweetener, including, for example, sugar, from 0.1 to 60% Vitamin C and from 2 to 15% sodium sulfite (in a preservative effective amount). Diluent or carrier is optionally present in amount ranging from 1% by weight to 99% by weight. In a preferred case, the keratin ingredient comprises S-sulfonated keratin intermediate filament protein. The cellulose and/or derivative thereof can be, for example, microcrystalline cellulose; the sweetener can be, for example, sugar, maltodextrin, sucrose, glucose syrup or artificial sweetener.

A preferred composition to promote skin cell growth is SIFP (see Tables 1 and 2). SIFP has been assigned CAS Number 68238-35-7. It is usually used herein in aqueous solution, i.e., dissolved in water (CAS Number 7732-18-5) and is preferably present in the aqueous solution at a level of 5% by weight.

In general, the dosage for the keratin ingredient ranges, for example, from 10 mg to 35 gm/day.

Dosage for powders ranges, for example, from 20-500 mg/day, more preferably 50-150 mg. For a 50:50 SIFP:stabilizer, a preferred daily dosage is 200 mg or 100 mg twice a day.

For protein solutions, the concentration can range, for example, to 5-25% added to a drink in amount up to about 50%, e.g., 2-10% giving a dosage of 0.1% keratin ingredient to 12.5% keratin ingredient. In a supplement drink of 250 ml, this gives 0.25 g to 31.25 g of keratin ingredient (e.g., SIFP or SPEP).

For antioxidant effect, keratin ingredient, preferably S-sulfonated keratin intermediate filament protein, S-sulfonated keratin high sulfur protein and/or S-sulfonated peptide is orally administered to a subject in need thereof in the form of composition of the first embodiment or as a drug producing antioxidant activity equal to 200-2200 μmol TEAC/100 g or 100 ml, to a subject (patient) in need of prophylaxis or treatment of a condition treated by administration of cysteine, N-acetyl cysteine and/or glutathione, e.g., for prophylaxis or treatment of the disorders mentioned in association with description of the third embodiment herein, in a therapeutically effective amount, e.g., in the dosages mentioned above.

Turning now to the second embodiment herein, it is directed to the use in human or veterinary medicine of oral supplement and nutraceutical composition as described above in a dosage of keratin ingredient ranging from 10 mg to 35 gm/day.

Turning now to the third embodiment herein, it is directed to oral administration of oral supplement or nutraceutical composition as described above in a prophylaxis or therapeutically effective dosage of keratin ingredient ranging from 10 mg to 35 gm/day to a patient (subject) in need of said prophylaxis or treatment for the prophylaxis or treatment of conditions or disorders caused by or associated with oxidative stress; e.g., conditions for which cysteine, N-acetyl cysteine and/or glutathione is administered for prophylaxis or amelioration of oxidative stress; e.g., respiratory diseases, angina pectoris, colon cancer, AIDS/HIV, breast cancer, acetaminophen poisoning, cervical dysplasia, acute respiratory distress syndrome, protection of kidney from x-ray damage, Sjogren's syndrome, oral, laryngeal, or lung cancer, hepatitis C, hearing improvement, eye disorder, heavy metal toxins, toxic by-products of smoking, smog, alcohol and fats, autism and joint ailments, for antioxidant effect, e.g., to reduce oxidative stress, for anti-inflammatory effect, for cognitive assistance, for skin whitening, to promote hair growth and for total body health.

Turning now to the fourth embodiment herein, it is directed to a method for prophylaxis or treatment of a patient (subject) with an inflammatory disorder, e.g., degenerative joint disease, such as rheumatoid arthritis or osteoarthritis; asthma, Crohn's disease, pelvic inflammatory disorder, acne inflammatory disorder, atherosclerosis, comprising oral administration to said patient of a therapeutically effective amount of keratin ingredient in an amount ranging from 10 mg to 35 gm/day, e.g., in a form of a nutraceutical composition or oral supplement composition of the first embodiment, to provide anti-inflammatory effect.

Turning now to the fifth embodiment herein, it is directed to promoting skin health in a patient (subject) in need thereof and comprises orally administering to said patient the composition of the first embodiment in an amount of keratin ingredient ranging from 10 mg to 35 g/day effective to promote skin health. In one case of the fifth embodiment copper is included in the composition of the first embodiment for administration in the fifth embodiment, e.g., in the form of copper complex of keratin ingredient. The copper can be included by preparing S-sulfonated keratin as described in Examples 1a and 1c of U.S. Publication No. 2005-0124797A1 and omitting purification after extraction to remove copper ions, e.g., omitting the copper ion sequestering step of Example 3a of U.S. Publication No. 2005-0124797A1 so that the product is copper complex of S-sulfonated keratin, e.g., to provide 0.2 to 1 mg copper per daily dose of oral supplement or nutraceutical composition herein. The copper stimulates metallothioneins, important regulators of skin cell growth and thereby potentiates skin replenishment and protects against skin damage, especially new skin damage.

In the sixth embodiment herein, S-sulfonated keratin intermediate filament protein is formulated into oral supplement or nutraceutical composition as described above.

The following examples illustrate formulations for compositions herein.

Keratin can be provided in a range of formulation types, illustrated by means of example. In each example, keratin is selected from the group illustrated above, including SIFP, SHSP, SPEP, SUHSP, SHGTP, IFP, HSP, PEP, UHSP, HGTP.

EXAMPLE 1a

Tablet containing keratin for reduction of oxidative stress, to provide anti-inflammatory effect and to promote skin health.

| Keratin ingredient | 50 mg |
|---|---|
| Microcrystalline cellulose | 145 mg |
| Starch | 50 mg |
| Magnesium stearate | 2.5 mg |
| Silica | 2.5 mg |

Are combined and compressed to form a tablet.

EXAMPLE 1b

Tablet containing keratin and synergistic material for reduction of oxidative stress, to provide anti-inflammatory effect and to promote skin health.

| Keratin ingredient | 50 mg |
|---|---|
| Vitamin C | 25 mg |
| Microcrystalline cellulose | 120 mg |
| Starch | 50 mg |
| Magnesium stearate | 2.5 mg |
| Silica | 2.5 mg |

Are combined and compressed to form a tablet.

EXAMPLE 2a

Hard gelatine capsule containing keratin for reduction of oxidative stress, to provide anti-inflammatory effect and to promote skin health.

| Keratin ingredient | 50 mg |
|---|---|
| Starch | 50 mg |

Are filled into hard gelatine capsules by conventional methods to create a keratin capsule.

EXAMPLE 2b

Hard gelatine capsule containing keratin and synergistic material for reduction of oxidative stress, to provide anti-inflammatory effect and to promote skin health.

| Keratin ingredient | 34 mg |
|---|---|
| Starch | 33 mg |
| Vitamin C | 33 mg |

Are filled into hard gelatine capsules by conventional methods to create a keratin capsule.

EXAMPLE 3

Soluble powder for drink or food additive useful for reduction of oxidative stress, to provide anti-inflammatory effect and to promote skin health.

Keratin powder, prepared by spray drying processes, is provided for direct addition to food, beverage or water as a supplement. The powder sachet contains 100 mg keratin ingredient, 100 mg vitamin C and 1 g maltodextrin.

EXAMPLE 4

Concentrated keratin liquid supplement, useful for reduction of oxidative stress, to provide anti-inflammatory effect and to promote skin health.

An aqueous solution containing 5% keratin is provided as a concentrated liquid sachet for addition to food, beverage or water. The concentrated liquid contains keratin ingredient and as a preservative, sodium sulfite.

EXAMPLE 5

Keratin supplement liquid drink useful for reduction of oxidative stress, to provide anti-inflammatory effect and to promote skin health.

A 250 ml beverage is provided containing the following ingredients.

| Keratin ingredient | 2.5 g |
|---|---|
| Sucrose | 10 g |
| Vitamin C | 1 g |
| Colour | <1 g |
| Flavour enhancer | <1 g |

EXAMPLE 6

Keratin gel supplement useful for reduction of oxidative stress, to provide anti-inflammatory effect and to promote skin health.

A keratin gel, containing 10% keratin protein in water and as a preservative, sodium sulfite, is provided as an ingestible supplement.

EXAMPLE 7a

Soft gelatine capsule containing keratin for reduction of oxidative stress, to provide anti-inflammatory effect and to promote skin health.

The keratin gel of Example 5 is filled into soft gelatine capsules by conventional processes to provide a supplement.

EXAMPLE 7b

Soft gelatine capsule containing keratin and a synergistic material for reduction of oxidative stress, to provide anti-inflammatory effect and to promote skin health.

The keratin gel of Example 6 containing also 10% vitamin C is filled into soft gelatine capsules by conventional processes to provide a supplement.

EXAMPLE 8

Chewing gum useful for reduction of oxidative stress, to provide anti-inflammatory effect and to promote skin health.

A one gram piece contains the following ingredients:

| | |
|---|---|
| Keratin ingredient | 50 mg |
| Gum base | 200 mg |
| Sugar | 580 mg |
| Glucose syrup | 160 mg |
| Flavor | 10 mg |

EXAMPLE 9

Dissolvable strip, useful for reduction of oxidative stress, to provide anti-inflammatory effect and to promote skin health.

A 76.6 mg quick dissolvable strip contains:

| | |
|---|---|
| Keratin ingredient | 30 mg |
| Film forming base | 21.5 mg |
| Essential oils | 6 mg |
| Plasticizing agents | 9 mg |
| Sweeteners | 5 mg |
| Surfactants | 1 mg |
| Flavorings | 4 mg |
| Preservative | 0.1 mg |
| Colorants | <0.1 mg |

EXAMPLE 10

Sublingual Tablet useful for reduction of oxidative stress, to provide anti-inflammatory effect and to promote skin health.

A 100 mg sublingual tablet contains:

| | |
|---|---|
| Keratin ingredient | 6 mg |
| Sugar | 6 mg |
| Cellulose | 87 mg |
| Flavor | <1 mg |

EXAMPLE 11

Lozenge useful for reduction of oxidative stress, to provide anti-inflammatory effect and to provide skin health.

A 1590 mg tablet contains:

| | |
|---|---|
| Keratin ingredient | 6 mg |
| Sugar | 1500 mg |
| Stearic acid | 75 mg |
| Magnesium stearate | 7.5 mg |
| Flavor | <1 mg |

Benefits of Keratin, Keratin Fractions, Etc.

Keratin proteins are characteristically rich in the sulfur amino acid cystine, and are one of the richest natural sources of cystine available. Cystine is readily converted to cysteine under reducing conditions. Cysteine has antioxidant capacity similar to that of glutathione, with reduction potentials of −230 mV and −240 mV respectively. As a source of sulfur rich amino acids keratin can act as an antioxidant. Furthermore, by providing essential components for the biochemical synthesis of glutathione, (cystine, glutamic acid and glycine), keratin can influence important antioxidant pathways in the body. Perhaps the earliest recorded use of keratin in human health is reference to XueYuTan, or Crinis Carbonisatus, which is charred keratin from human hair; XueYuTan has been used for centuries to accelerate blood clotting in traditional Chinese medicine.

Conventional methods of isolating keratin from natural sources involve hydrolysis using acid, alkali or enzymatic conditions. This typically results in substantial degradation to the protein, and the resulting peptides are typically significantly lower in cystine content than their source keratin. For example, cystine can be irreversible degraded to form cysteic acid or lanthionine under acid or alkaline conditions. Intact proteins that are not hydrolyzed maintain their cystine content, and so are a preferred source of keratin for ingestion and can play a more active role in the effect redox related pathways in the body.

S-sulfo cysteine is a derivative of cysteine that provides reversible modification to the cysteine group. This prevents the oxidation of two neighboring cysteine species to form cystine, whilst still maintaining a reactivity towards oxidants. This is demonstrated by the antioxidant capacity of s-sulfo keratin derivatives.

Keratin protein fractions can have a higher individual content of cystine than the source keratin, and so be advantageous when used to effect the body's redox pathways. For example, the high sulfur protein fraction HSP can have a cystine content of up to 22 mol %.

Keratin, in particular intact keratin protein fractions, can benefit a range of health conditions. This includes those which have been linked to redox pathways in the body and have been linked to some benefits associated with cysteine, N-acetyl cysteine (NAC) or glutathione supplementation, for example:

1. Respiratory diseases[2-6]

A number of studies had shown that cysteine and its derivatives can help dissolve mucus, loosen phlegm and improve symptoms associated with chronic bronchitis, asthma, cystic fibrosis and emphysema. Chronic smokers also can benefit from cysteine derivative supplementation. Studies, involving a total of about 1,400 individuals, suggest that NAC taken daily at a dose of 400 to 1,200 mg can reduce the number of acute attacks of severe bronchitis.

2. Angina Pectoris

Cysteine derivatives can reduce incidence of heart attacks and other severe heart problems when combined with nitroglycerin[7].

3. Colon Cancer Prevention

A double-blind placebo-controlled study showed potential anticancer benefits of NAC treatment. Taking NAC at 800 mg daily for 12 weeks resulted in observations of more normal cells in biopsy tissue as compared to those in the placebo group[8].

4. AIDS/HIV

CD4 lymphocytes are known to decline with the progression of AIDS. Many treatment modalities incorporate procedures to enhance immune function, including the evaluation and monitoring of glutathione and CD4 lymphocyte function.

Cysteine derivatives may increase levels of CD4 cells in healthy people and slow CD4+ cell decline in people with HIV[9,10].

5. Breast Cancer

Zhang et al conducted a prospective nested case-control study among 32,826 women who provided blood specimens during 1989-1990. They found higher plasma total cysteine concentrations were significantly associated with a lower risk of breast cancer. The findings from this prospective study suggest that higher plasma concentrations of total cysteine predict a reduced risk of breast cancer. Cysteine or its precursors might have the potential to be chemopreventive against breast cancer[11].

6. Acetaminophen (Paracetamol) Poisoning[12,13]

NAC is commonly administered oral or intravenous to prevent or reduce liver and kidney damage associated with overdose of acetaminophen.

7. Cervical Dysplasia

Cervical dysplasia is a premalignant or precancerous change to the cells of the cervix. Low levels of cysteine may be linked to an increased risk of cervical dysplasia[14].

8. Acute Respiratory Distress Syndrome

Cysteine derivatives may be helpful in acute respiratory distress syndrome by increasing the lungs surfactants[15].

9. Protection of the Kidney

Radiologists often administer contrast agents in order to get more information from certain types of x-rays which can be damaging to the kidney. Cysteine derivatives can help protect the kidney from such damage[16].

10. Sjogren's Syndrome

This syndrome is an autoimmune condition in which the immune system destroys moisture-producing glands. Thus, patients have following symptoms, dry eyes, dry mouth, difficulty swallowing, severe dental cavities caused by dry mouth, oral yeast infections, and vaginal dryness, etc. When NAC is administered, it helps the body make antioxidant enzyme glutathione. It is also thought to help loosen secretions, and for this reason it has been tried as a treatment for Sjogren's syndrome[17].

11. Cancer Prevention

European Organization of Research and Treatment of Cancer (EORTC) chemoprevention study chose NAC in curatively treated patients with oral, laryngeal, or lung cancer because NAC is showed the ability to exert protective effects, including extracellular inhibition of mutagenic agents from exogenous and endogenous sources, inhibition of genotoxicity of reactive oxygen species, modulation of metabolism coordinated with blocking of reactive metabolites, protection of DNA and nuclear enzymes, and prevention of the formation of carcinogen-DNA adducts. NAC has also demonstrated an effect on mutagen-induced chromosomal sensitivity assays, and on anticarcinogenicity in experimental animal models. In addition, preliminary data from EUROSCAN show good compliance in treated patients and a low frequency of side effects (18).

12. Hepatitis C

Hepatitis C virus is an RNA virus that replicates in both the liver and lymphoid cells. Interferon-alpha (IFN) is a useful treatment of chronic hepatitis C. However, resistance to IFN occurs frequently. NAC administrated to IFN-unresponsive patients resulted in an improvement in liver enzyme activity in all patients, with complete normalization in 41% of cases after 5-6 months of combined therapy[19]. Administration of NAC alone for 1 month was without effect in the patients that were not receiving IFN[19].

13. Hearing Improvement

Cysteine derivatives have been found to prevent damage to the inner ear by chemotherapy in the laboratory[20]. Balli et al. found NAC may be useful in enhancing the functional effects of surgery in serous otitis media. They found hearing had improved more significantly in the group taking NAC than in the control group. These findings indicated the pharmacological effect of oral NAC in the middle ear, and showed that it enhanced recovery of hearing[21].

The three main causes of hearing loss are noise, ototoxic drugs and aging. All of these involve the common factor of oxidative stress, either through increased free radical formation or reduced antioxidant availability. Therefore, cysteine derivatives, as antioxidants, have the potential to reduce hearing loss.

14. Eye Disorders

Cysteine derivatives may be beneficial for individuals with chronic posterior blepharitis, a common inflammatory condition of the inner eyelid. The abnormality of the tear film that occurs in people with blepharitis may be a result of oxidation damage of certain key molecules produced by the meibomian glands; resulting in increased evaporation of tears and dryness and irritation of the eyes. NAC protects the tear film by increasing glutathione levels in the eye[22].

15. Detoxification Effects

L-cysteine can help neutralize heavy metal toxins and toxic by-products of smoking, smog, alcohol and fats[23]. Toxic metals such as lead, arsenic, cadmium, and mercury, usually will find their way to the liver. The liver then binds the metals with cysteine and other amino acids and releases them into the bile, which will find its way to the bowel[24]. Under normal circumstances, the metals are usually re-absorbed back into the system. Cysteine and other amino acid can bind to heavy metals and carry them out of the body.

16. Autism

Autism, which occurs in approximately 15 of 10,000 individuals, is a developmental disability and affects functioning of the brain. Cysteine can stabilize the secretin preparation and may help autistic children who are receiving secretin[25].

17. Joint Ailments

Antioxidants have been known to be essential for joint health for a long time (Grimble, 1994; Homandberg et al., 1996; Parcell, 2002; Zafarullah et al., 2003). Antioxidants primarily help prevent joint breakdown and aid in joint repair. The cysteine in keratin is vital in maintaining the anti oxidant status within the joint and also prevents new situations of oxidative stress causing damage.

New proteins are always needed to maintain joints in good repair. Keratin provides an excellent source of cysteine and essential amino acids required to make new joint proteins (Muller et al., 1998).

Aged joints and joints with diseases like arthritis exhibit defective cysteine metabolism (Bradley et al., 1994; Wojtecka-Lukasik et al., 2002). Cysteine is especially important for joint health because increasing cysteine increases cysteine dioxygenase (CDO) levels, an enzyme which generates natural inorganic sulphate and ultimately taurine from cysteine (Wilkinson and Waring, 2002; Tappaz, 2004). Natural sulfur generated from keratin by CDO is used for sulfation (see 4. below) but taurine itself is an important anti-inflammatory. Taurine scavenges hypochlorous acid generated by neutrophils and the resultant taurine-Cl is an anti-inflammatory compound that is deficient in arthritic patients for example (Kontny et al., 2002). Keratin ingredient increases the anti-inflammatory taurine-Cl, helping reduce joint inflammation.

Proteoglycans are sugar-protein polymers in our joints which are required for joint mobility and strength and especially, resistance to compression (Roughley and Lee, 1994). Heavy sulfation of joint proteoglycans occurs naturally and without sulfation joints deteriorate (Rossi et al., 2003). Sulfation of proteoglycans is catalysed by sulfotransferases (Kusche-Gullberg and Kjellen, 2003; Rath et al., 2004), which catalyse the transfer of sulfur from 3'-phosphoadenosine 5'-phosphosulfate (PAPS) to proteoglycans and other molecules. Inorganic sulfur is required to form PAPS by the PAPS synthase enzyme (Venkatachalam, 2003). This sulfur can be sourced from cysteine-rich keratin ingredient as the cysteine is broken down by CDO.

18. Antioxidant Effect

It has been established that anti-oxidants are essential for good health and diets deficient in natural anti-oxidants or disease states can deplete the bodies natural reserves of antioxidants (1. Heyland, D. K., Dhaliwal, R., Suchner, U., and Berger, M. M. Antioxidant nutrients: a systematic review of trace elements and vitamins in the critically ill patient. Intensive Care Med, 31: 327-337, 2005. 2. Elsayed, N. M. Antioxidant mobilization in response to oxidative stress: a dynamic environmental-nutritional interaction. Nutrition, 17: 828-834, 2001.) Keratin ingredient is shown herein to have antioxidant activity.

19. Anti-Inflammatory Effect

Figure 7:
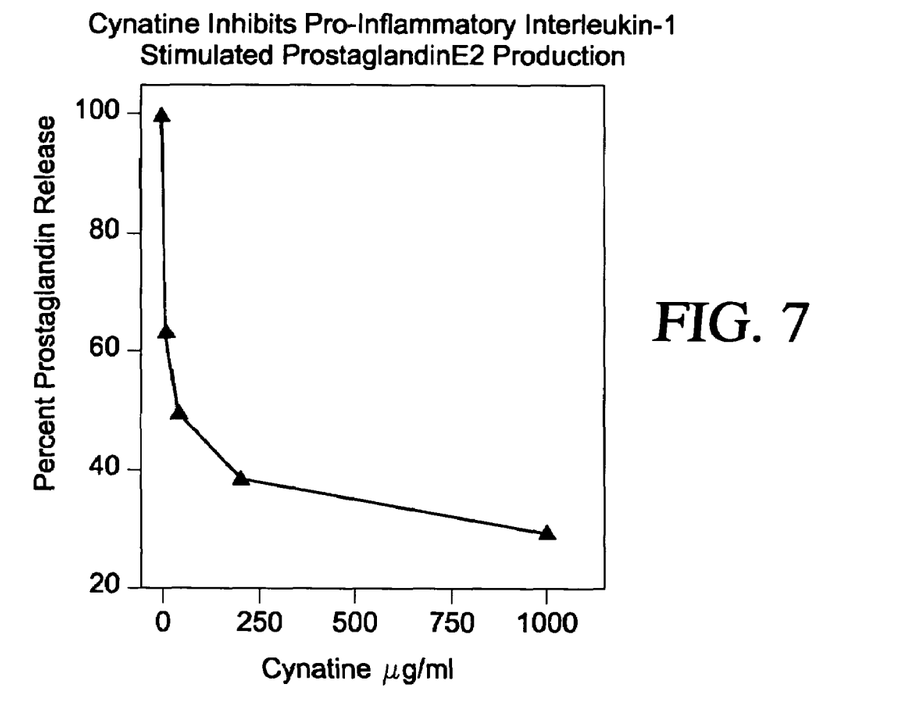
FIG. 7 is a graph of Cynatine (SIFP) concentration versus percent prostaglandin release and shows results of Background Example 2.

Inflammation occurs in a broad spectrum of disease states and is a leading cause of morbidity (1. Serhan, C. N. and Savill, J. Resolution of inflammation: the beginning programs the end. Nat Immunol, 6: 1191-1197, 2005. 2. Henson, P. M. Dampening inflammation. Nat Immunol, 6: 1179-1181, 2005.). Keratin ingredient suppresses prostaglandinE2 (PGE2) in response to inflammatory interleukin-1 (IL-1) (FIG. 7). IL-1 stimulation of PGE2 is a characteristic of inflammation and is blocked by well known anti-inflammatories like indomethacin and COX-2 inhibitors (Verbruggen, G. Chondroprotective drugs in degenerative joint diseases. Rheumatology (Oxford), 2005.). For comparative purposes, for example in joint disease, glucosamine caused a 76% and a 68% PGE2 reduction (Largo, R., Alvarez-Soria, M. A., Diez-Ortego, I., Calvo, E., Sanchez-Pernaute, O., Egido, J. and Herrero-Beaumont, G. Glucosamine inhibits IL-1beta-induced NFkappaB activation in human osteoarthritic chondrocytes. Osteoarthritis Cartilage JT—Osteoarthritis and cartilage/OARS, Osteoarthritis Research Society., 11:290-298, 2003. Chan, P. S., Caron, J. P., Rosa, G. J. and Orth, M. W. Glucosamine and chondroitin sulfate regulate gene expression and synthesis of nitric oxide and prostaglandin E(2) in articular cartilage explants. Osteoarthritis Cartilage JT—Osteoarthritis and cartilage/OARS, Osteoarthritis Research Society., 13:387-394, 2005.), chondroitin alone and glucosamine and chondroitin together caused a 50% and 76% reduction in PGE2, respectively (Chan, P. S., Caron, J. P., Rosa, G. J. and Orth, M. W. Glucosamine and chondroitin sulfate regulate gene expression and synthesis of nitric oxide and prostaglandin E(2) in articular cartilage explants. Osteoarthritis Cartilage JT—Osteoarthritis and cartilage/OARS, Osteoarthritis Research Society., 13:387-394, 2005.).

20. Skin Health

ROS are known to cause skin damage (e.g., sun damage). In addition, defective moisture barrier effect just below the outer surface of the skin leads to drying out of the skin. Both of these cause defective skin tone and can cause the skin to have an unhealthy appearance and/or dull cast. The invention herein prevents or treats these effects by promoting skin cell proliferation, by promoting increased antioxidant effect, by potentiating formation and maintenance of a moisture barrier just below the outer skin surface and by promoting skin tone and radiance. The promotion of skin cell proliferation also has the effect of promoting wound healing. Wound healing is promoted by the invention herein by the stimulation of skin cell growth, by providing increased antioxidant effect to accelerate healing, by supplying keratin building blocks for potentiating moisture barrier formation and healing and by providing a good source of cysteine (from cystine) needed by skin especially during healing and to provide sulfur for potentiating skin metabolism and skin cell division and growth.

21. Cognitive Assistance

High anti-oxidant activity is associated with cognitive ability (1. Rassin, D. K. and Smith, K. E. Nutritional approaches to improve cognitive development during infancy: antioxidant compounds. Acta Paediatr Suppl, 92: 34-41, 2003. 2. Milgram, N. W., Head, E., Muggenburg, B., Holowachuk, D., Murphey, H., Estrada, J., Ikeda-Douglas, C. J., Zicker, S. C., and Cotman, C. W. Landmark discrimination learning in the dog: effects of age, an antioxidant fortified food, and cognitive strategy. Neurosci Biobehav Rev, 26: 679-695, 2002.). With inherent antioxidant activity (FIG. 3) and the ability to stimulate the bodies own natural anti-oxidant enzymes (FIGS. 1, 2, 4), keratin ingredient is considered to have the ability to increase cognitive ability. An alternative use in this general area is treatment of patients with neuro-degenerative disease including, but not limited to, Alzheimers (1. Brugge, K. L., Nichols, S., Delis, D., Saitoh, T., and Truaner, D. The role of alterations in free radical metabolism in mediating cognitive impairments in Down's syndrome. EXS, 62: 190-198, 1992.) and Downs Syndrome (1. Brugge, K. L., Nichols, S., Delis, D., Saitoh, T., and Truaner, D. The role of alterations in free radical metabolism in mediating cognitive impairments in Down's syndrome. EXS, 62: 190-198, 1992.) which are both diseases where the anti-oxidant and cysteine derivative glutathione has been implicated as a therapeutic agent.

22. Skin Whitening

Keratin ingredient is a rich source of cysteine and is considered to have the ability to alter skin pigment synthesis, resulting in skin whitening. The pigment in our skin is composed of eumalanin, or dark pigment, and pheomelanin, or light pigment. In the presence of cysteine, production of pigment switches from dark to light pigment (1. del Marmol, V.; Ito, S.; Bouchard, B.; Libert, A.; Wakamatsu, K.; Ghanem, G.; Solano, F. Cysteine deprivation promotes eumelanogenesis in human melanoma cells. *J Invest Dermatol* 1996, 107, (5), 698-702. 2. Smit, N. P.; Van der, M. e. H.; Koerten, H. K.; Kolb, R. M.; Mommaas, A. M.; Lentjes, E. G.; Pavel, S. Melanogenesis in cultured melanocytes can be substantially influenced by L-tyrosine and L-cysteine. *J Invest Dermatol* 1997, 109, (6), 796-800. 3. Fujiwara, Y.; Sahashi, Y.; Aritro, M.; Hasegawa, S.; Akimoto, K.; Ninomiya, S.; Sakaguchi, Y.; Seyama, Y. Effect of simultaneous administration of vitamin C, L-cysteine and vitamin E on the melanogenesis. *Biofactors* 2004, 21, (1-4), 415-418.). The major enzyme regulating pigment production is tyrosinase, which converts tyrosine to dopaquinone which can then go on to form either pigment. Tyrosinase is generally inhibited by antioxidants, including the major intracellular antioxidant, glutathione (4. Kong, K. H.; Park, S. Y.; Hong, M. P.; Cho, S. H. Expression and characterization of human tyrosinase from a bacterial expression system. *Comp Biochem Physiol B Biochem Mol Biol* 2000, 125, (4), 563-569. 5. Yamamura, T.; Onishi, J.; Nishiyama, T. Antimelanogenic activity of hydrocoumarins in cultured normal human melanocytes by stimulating intracellular glutathione synthesis. *Arch Dermatol Res* 2002, 294, (8), 349-354.). Interestingly, glutathione requires cysteine for its synthesis as cysteine comprises one third of glutathione.

23. Hair Growth

Growth of hair requires healthy hair follicle cells and an adequate supply of amino acids with abundant cysteine (1. Alonso, L.C. and Rosenfield, R.L. Molecular genetic and endocrine mechanisms of hair growth. Horm Res, 60: 1-13, 2003.). Keratin ingredient meets these criteria and is considered to have the ability to stimulate cell and hair growth and has a mix of amino acids suitable for hair production.

REFERENCES (1) J W Olney, O L Ho. (1970). Brain damage in infant mice following oral intake of glutamate, aspartate or cysteine. *Nature* 1970; 227:609-10.

(2) G C Riise, et al. (1994). The intrabronchial microbial flora in chronic bronchitis patients: a target for N-acetylcysteine therapy? *European Respiratory Journal*. 7:94-101.

(3) E M Grandjean, et al. (2000). Efficacy of oral long-term N-acetylcysteine in chronic bronchopulmonary disease: a meta-analysis of published double-blind, placebo-controlled clinical trials. *Clinical Therapy*. 22:209-221.

(4) N C G Hansen, et al. (1994). Orally administered N-acetylcysteine may improve general well-being in patients with mild chronic bronchitis. *Respiratory Medicine*. 88:531-535.

(5) J B Rasmussen, C Glennow. (1988). Reduction in days of illness after long-term treatment with N-acetylcysteine controlled-release tablets in patients with chronic bronchitis. *European Respiratory Journal*. 1:351-355.

(6) G D Parr, A Huitson. (1987). Oral fabrol (oral N-acetylcysteine) in chronic bronchitis. *British Journal of Diseases of Chest*. 81:341-348.

(7) D Ardissino, et al. (1997). Effect of transdermal nitroglycerin or N-acetylcysteine, or both, in the long-term treatment of unstable angina pectoris. *Journal of the American College of Cardiology*. 29:941-947.

(8) R D Estensen, et al. (1999). N-acetylcysteine suppression of the proliferative index in the colon of patients with previous adenomatous colonic polyps. *Cancer Letters*. 147:109-114.

(9) R Kinscherf, et al. (1994). Effect of glutathione depletion and oral N-acetylcysteine treatment on CD4+ and CD8+ cells. *FASEB Journal*. 8:448-451.

(10) B Akerlund, et al. (1996). Effect of N-acetylcysteine (NAC) treatment on HIV-1 infection: a double-blind placebo-controlled trial. *European Journal of Clinical Pharmacology*. 50:457-461.

(11) Shumin Zhang, et al. (2003). A prospective study of plasma total cysteine and risk of breast cancer. *Epidemiology Biomarkers & Prevention*. 12, 1188-1193.

(12) LP James, et al. (2003) Effect of N-Acetylcysteine on Acetaminophen Toxicity in Mice: Relationship to Reactive Nitrogen and Cytokine Formation. *Toxicological Sciences* 75(2): 458-467.

(13) K Shankar, et al. (2003). Type 1 Diabetic Mice Are Protected from Acetaminophen Hepatotoxicity. *Toxicological Sciences*. 73(2): 220-234.

(14) M T Goodman. (2000). Case-control study of plasma folate, homocysteine, vitamin B12, and cysteine as markers of cervical dysplasia. *Cancer*. 89(2):376-382.

(15) G R Bernard, et al. (1997). A trial of antioxidants N-acetylcysteine and procysteine in ARDS. The Antioxidant in ARDS Study Group. *Chest*. 112:164-172.

(16) M Tepel, et al. (2000). Prevention of radiographic-contrast-agent-induced reductions in renal function by acetylcysteine. *New England Journal of Medicine*. 343:180-184.

(17) M T Walters, et al. (1986). A double-blind, cross-over, study of oral N-acetylcysteine in Sjogren's syndrome. *Scand J Rheumatol Suppl*. 61:253-258.

(18) N De Vries, S De Flora. (1993). N-acetyl-1-cysteine. *Journal of Cellular Biochemistry*. Supplement. 17F:270-277.

(19) O Beloqui, et al. (1993). N-acetyl cysteine enhances the response to interferon-alpha in chronic hepatitis C: a pilot study. *Journal of Interferon Research*. 13:279-282.

(20) J G Feghali, et al. (2001) L-n-acetyl-cysteine protection against cisplatin-induced auditory neuronal and hair cell toxicity. *Laryngoscope*. 111(7):1147-55.

(21) R Balli. (1980). Controlled trial on the use of oral acetylcysteine in the treatment of glue-ear following drainage. *European Journal of Respiratory Diseases*. 61, Suppl 111; 158.

(22) E Yalcin, et al. (2002). N-acetylcysteine in chronic blepharitis. *Cornea*. 21:164-168.

(23) S De Flora, et al. (2001). Mechanisms of N-acetylcysteine in the prevention of DNA damage and cancer, with special reference to smoking-related end-points. *Carcinogenesis*, 22(7): 999-1013.

(24) E R Braverman, et al ed. (2003). *The healing nutrients within: facts, findings, and new research on amino acids*. Basic Health Publications Inc.

(25) S L Connors, et al. (1999). Secretin and autism: the role of cysteine. *Journal of the American Academy of Child and Adolescent Psychiatry*. 38:795-796.

(26) J K Apple, C B Boger, D C Brown, C V Mxwell, K G Friessen, W J Roberts, Z B Johnson. Effect of feather meal on live animal performance and carcass quality and composition of growing finishing swine, *J. Anim. Sci*. 81: 172-81, 2003.

(27) T W Loy, G P Lardy, M L Bauer, W D Slanger, J S Caton. Effects of supplementation on intake an growth of nursing calves grazing native range in southeastern North Dakota, *J. Anim. Sci* 80: 2717-25, 2002.

BACKGROUND EXAMPLE 1

Antioxidant Potential

The antioxidant potential of a range of keratin protein fractions has been determined. This illustrates the direct potency of each material, but does not indicate the indirect influence of the material on redox pathways.

Sample Preparation

Liquid samples were diluted with assay buffer as required. Powder samples were weighed out (approx 10 mg) and dissolved in assay buffer (1 mL), then further diluted as appropriate. Duplicate preparations were made for each extract.

Antioxidant Activity

Antioxidant activity was measured using the ABTS radical scavenging assay. This assay system is based on generating a free radical (which is coloured) and the ability of an extract to quench the radical and return it to a non-coloured "harmless" form. This method compares antioxidant activity of the extracts to Trolox, a water-soluble vitamin E analogue. Results were expressed as the amount of Trolox equivalent antioxidant capacity (TEAC) per hundred gram, or milliliters, of sample (µmol TEAC/100 g or µmol TEAC/100 mL), which represents the amount of Trolox (vitamin E) that gives the same response as one hundred grams or mLs, of sample. Triplicate analyses (at different concentrations) were carried out on each extract.

Results:

The antioxidant activity of the samples is shown in Table 3.

TABLE 3

Antioxidant activity of keratin protein and peptide fractions

| Sample | Protein/peptide content % w/w | Antioxidant activity |
|---|---|---|
| SPEP | 15 | 281.86 µmole TEAC/100 mL |
| SIFP Solution | 5 | 207.92 µmole TEAC/100 mL |
| SHSP | 50 | 850 µmole TEAC/100 g |
| SIFP powder | 97 | 2196 µmole TEAC/100 g |

Table 3 shows good antioxidant activity for SPEP, SIFP (as powder or solution) and SHSP.

BACKGROUND EXAMPLE 2

The anti-inflammatory activity of S-sulfonated intermediate filament protein has been determined. Evaluation is carried out by interleukin-1 (IL-1) induced prostaglandin E2 (PGE2) release from Wi 38 human lung fibroblast cells at test concentrations of 8, 40, 200, 1000 and 5000 µg/ml. No effect is observed in the absence of IL-1. Results are shown in FIG. 7 (Cynatine refers to SIFP). The results demonstrate that S-sulfonated intermediate filament protein is as effective as glucosamine and chondroitin in reducing PGE2 release.

BACKGROUND EXAMPLE 3

Glutathione Peroxidase Activity

Glutathione Peroxidase is one of the body's antioxidant enzymes whose activity is known to be stimulated by antioxidants like vitamin E and selenium. Glutathione peroxidases catalyze the reduction of hydroperoxides in the presence of glutathione.

As used in this example, Cynatine refers to SIFP described previously.

Testing is carried out by feeding rats Cynatine. Dosage was 100 g per kg body weight given daily by gavage. Glutathione peroxidase activity in serum of rats fed Cynatine and in serum of control rats is measured by standard assay kit and glutathione peroxidase activity in serum in rats fed Cynatine was compared to glutathione peroxidase activity in serum of control rats.

Figure 1:
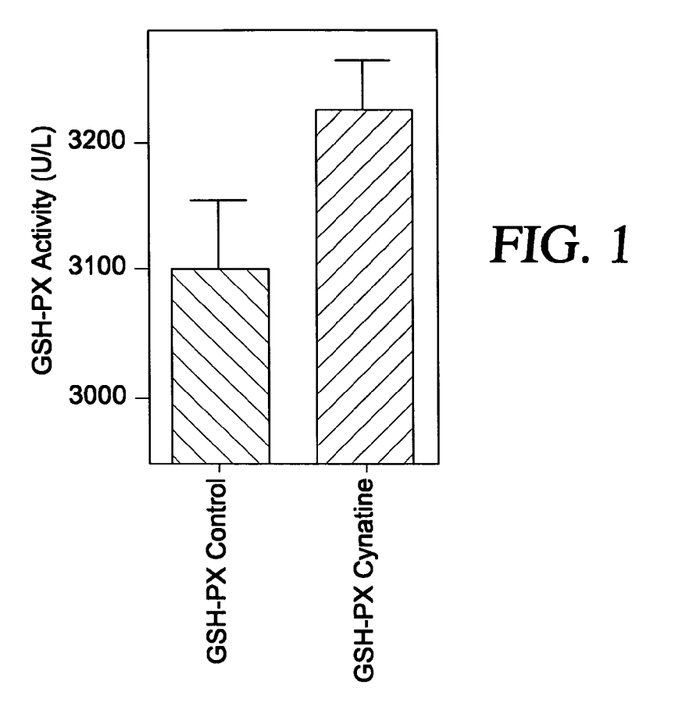
FIG. 1 is a comparison of glutathione-dependent peroxidase (GSH-PX) activity in serum from rats fed Cynatine (SIFP) to (-GSH-PX-) activity in serum of control rats and shows results of Background Example 3.

Results are shown in FIG. 1.

As shown in FIG. 1, Cynatine provides significantly greater GSH-PX activity compared to control.

BACKGROUND EXAMPLE 4

Superoxide Dismutase (SOD) Activity

Superoxide dismutase (SOD) is known to catalyze reduction of superoxide anions and thereby potentiate protection against ROS.

As used in this example, Cynatine refers to SIFP described previously.

Testing is carried out by feeding rats Cynatine at 100 g per kg body weight given daily by gavage. SOD activity in serum of rats fed Cynatine and in serum of control rats was determined by standard assay kit and SOD activity determined in serum of rats fed Cynatine is compared to SOD activity determined in serum of control rats.

Figure 2:
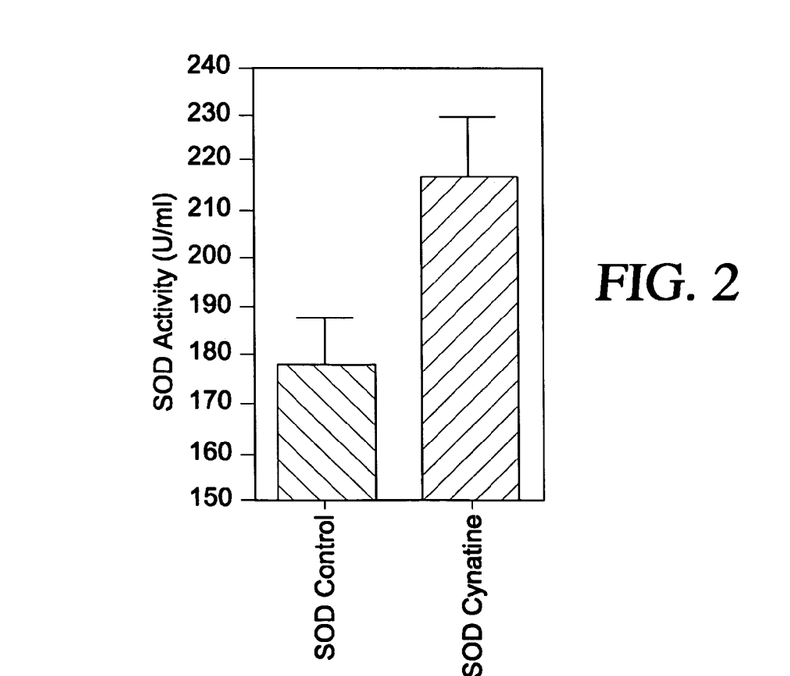
FIG. 2 is a comparison of superoxide dismutase (SOD) activity in serum from rats fed Cynatine (SIFP) to SOD activity in serum of control rats and shows results of Background Example 4.

Results are shown in FIG. 2.

As shown in FIG. 2, Cynatine provides significantly greater SOD activity compared to control.

BACKGROUND EXAMPLE 5

Antioxidant Activity

Antioxidant activity of Cynatine, kiwi fruit and broccoli was determined using the ABTS radical scavenging assay. This assay system is based on generating a free radical (which is coloured) and the ability of an extract to quench the radical and return it to a non-coloured "harmless" form. This method compares antioxidant activity of the extracts to Trolox, a water-soluble vitamin E analogue. Results are expressed as the amount of Trolox equivalent antioxidant capacity per hundred gram, or milliliters, of sample (µmol TEAC/100 g or µmol TEAC/100 mL), which represents the amount of Trolox (vitamin E) that gives the same response as one hundred grams or mLs, of sample. Triplicate analyses (at different concentrations) are carried out on each extract.

As used in this example, Cynatine refers to SIFP described previously.

Figure 3:
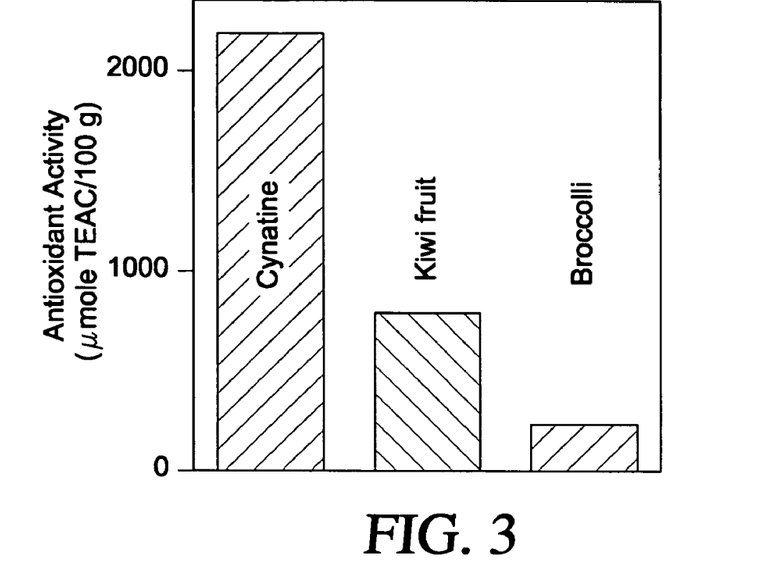
FIG. 3 is a comparison of antioxidant activity of Cynatine (SIFP), kiwi fruit and broccoli and shows results of Background Example 5.

Results are shown in FIG. 3.

As shown in FIG. 3, Cynatine provides more than twice as much antioxidant activity as kiwi fruit and more than six times as much antioxidant activity as broccoli.

BACKGROUND EXAMPLE 6

Reduction of Malondialdehyde (MDA) Level

Malondialdehyde (MDA) is known to be a marker of lipid peroxidation. Peroxidized lipids are known to damage proteins. MDA readily combines with functional groups of proteins and MDA-modified proteins are known to show altered physio-chemical behavior and antigenicity.

As used in this background example, Cynatine refers to SIFP described previously. Testing is carried out by feeding rats Cynatine at 100 g per kg body weight given daily by gavage and determining MDA levels in serum of rats fed Cynatine and in serum of control rats using a standard assay kit and comparing MDA level determined in serum or rats fed Cynatine and determined in serum of control rats.

Figure 4:
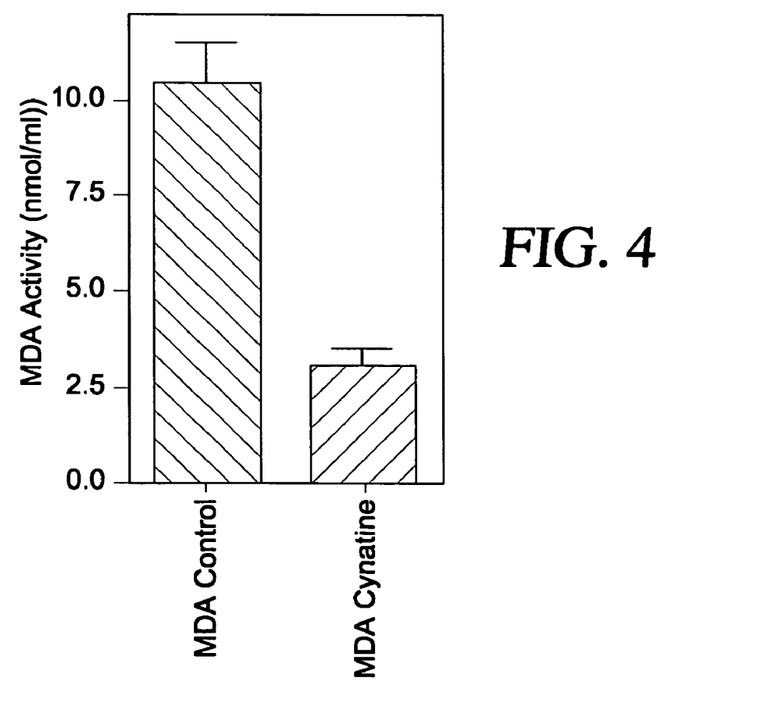
FIG. 4 is a comparison of malondialdehyde (MDA) levels in serum of rats fed Cynatine (SIFP) to MDA level in control rats and shows results of Background Example 6.

Results are shown in FIG. 4.

As shown in FIG. 4, MDA level in Cynatine fed rats is substantially less than in control rats.

BACKGROUND EXAMPLE 7

Cystine Contents

Cystine content of Cynatine (SIFP described previously), collagen/gelatin, casein and soy protein were extracted from published literature on the amino acid content of these proteins. Results are shown in FIG. 5

Figure 5:
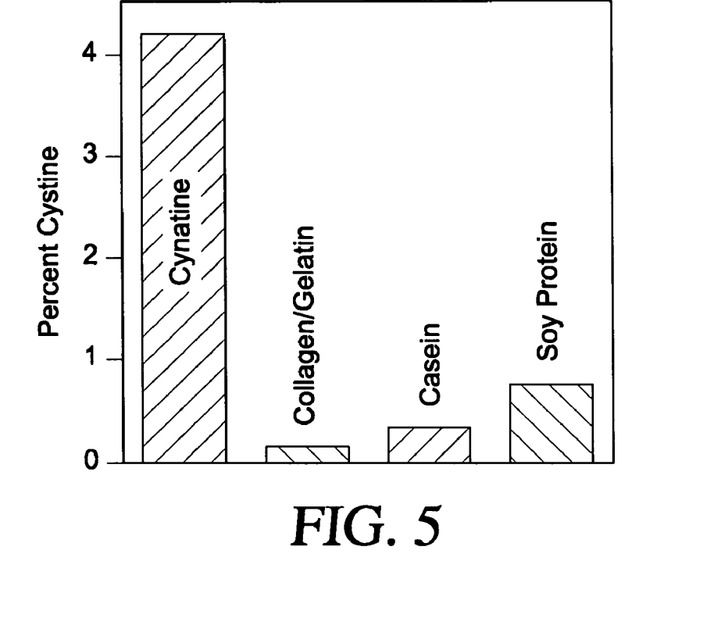
FIG. 5 compares cystine contents of Cynatine (SIFP) and other proteins and shows results of Background Example 7.

As shown in FIG. 5, Cynatine has much higher levels of cystine than the other proteins and thus provides much higher levels of cysteine (needed for healing) and sulfur necessary for metabolic turnover of skin.

BACKGROUND EXAMPLE 8

Stimulation of Keratinocyte Proliferation

Tests are carried out to determine the skin cell proliferation effect of Cynatine (SIFP) compared to control using the MTT assay of proliferative activity. The MTT assay is a well established assay of proliferation and recognized as such by those proficient in the art. Human keratinocyte skin cells are fed either Cynatine or cell media and cell proliferation measured in triplicate every day for three days.

Figure 6:
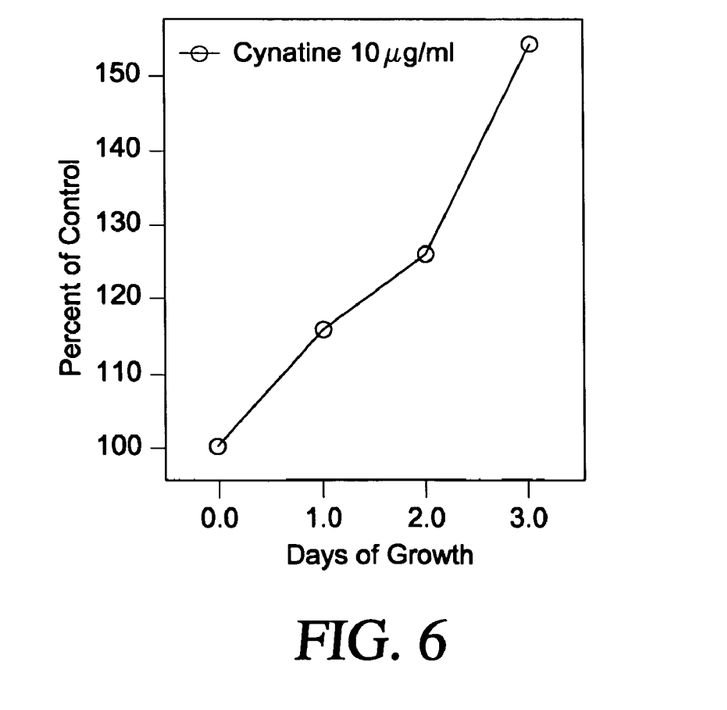
FIG. 6 is a graph of keratinocyte proliferation as a percent of control and shows results of Background Example 8.

FIG. 6 (Cynatine present at 10 μg/ml) shows that Cynatine stimulates proliferation of human skin cells up to 50%.

BACKGROUND EXAMPLE 9

Promotion of Hair Growth

Figure 8:
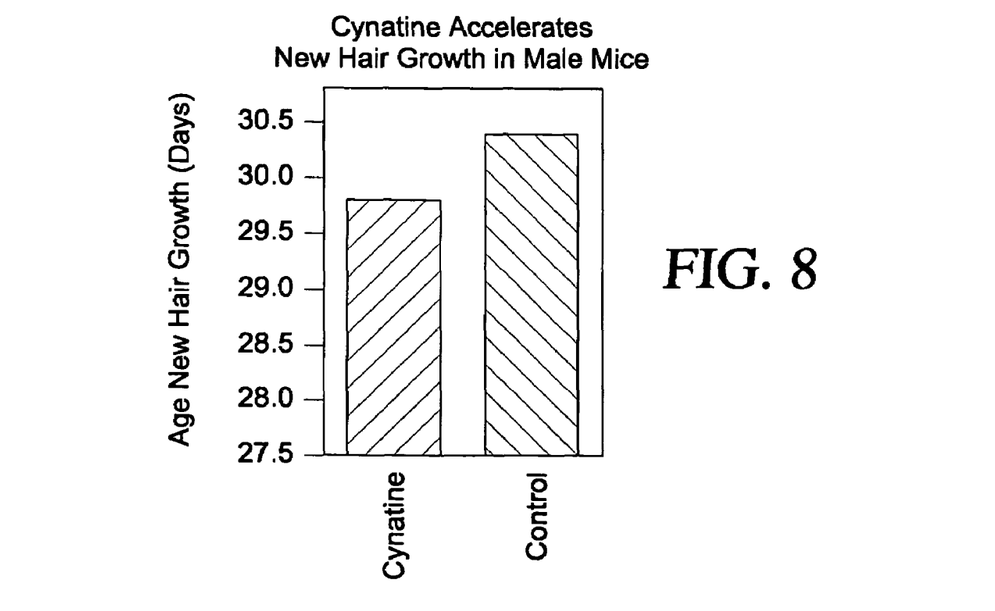
FIG. 8 is a graph of age of new hair emergence in male mice fed either keratin ingredient or control and shows results of Background Example 9.

Male mice fed Cynatine (SIFP) are shown to have accelerated hair growth. In a test commissioned by the assignee, male mice were fed an average of 4 g food per day with Cynatine (SIFP) comprising 5% of the diet (200 mg SIFP/day), and in the case of the control, the SIFP was replaced by an equal amount of skim milk powder. Results are shown in FIG. 8 where Cynatine is shown to accelerate new hair growth compared to control.

Cynatine can stimulate cell growth (see FIG. 6) and has a good mix of amino acids for hair production (Table 1).

EXAMPLE 12

A patient presents with cystic fibrosis. Oral administration of any of the compositions of Examples 1-11 in a dosage of keratin ingredient ranging from 10 mg to 35 gm/day helps dissolve mucous, loosen phlegm and improve symptoms associated with the cystic fibrosis.

EXAMPLE 13

A patient presents with emphysema. Oral administration of any of the compositions of Examples 1-11 in a dosage of keratin ingredient ranging from 10 mg to 35 gm/day helps dissolve mucous, loosen phlegm and improve symptoms associated with the emphysema.

EXAMPLE 14

A patient presents with asthma. Oral administration of any of the compositions of Examples 1-11 in a dosage of keratin ingredient ranging from 10 mg to 35 gm/day helps dissolve mucous, loosen phlegm and improve symptoms associated with the asthma.

EXAMPLE 15

A patient presents with rheumatoid arthritis. Methotrexate therapy is discontinued because of side effects. Oral administration of any of the compositions of Examples 1-11 in a dosage of keratin ingredient ranging from 10 mg to 35 gm/day causes stabilization of arthritic damage and amelioration of pain and reduces flare ups.

EXAMPLE 16

A patient presents with osteoarthritis. COX-2 inhibitor administration is discontinued because of heart health risk. Oral administration of any of the compositions of Examples 1-11 in a dosage of keratin ingredient ranging from 10 mg to 35 gm/day causes stabilization of joint damage and amelioration of pain.

EXAMPLE 17

A study at the University of Otago at Wellington, New Zealand demonstrates a 19% wound area after three days of treatment with Cynatine (SIFP) compared to a leading commercial dressing.

EXAMPLE 18

A study at AgResearch, Ruakura, New Zealand, demonstrates that keratin ingredient accelerates emergence of new male hair.

EXAMPLE 19

An individual wishing to improve her/his cognitive abilities supplements diet with keratin ingredient at 200 mg per day. Improvement in cognitive abilities is noted after thirty days.

Variations

The foregoing description of the invention has been presented describing certain operable and preferred embodiments. It is not intended that the invention should be so limited since variations and modifications thereof will be obvious to those skilled in the art, all of which are within the spirit and scope of the invention.

What is claimed is:

1. An oral supplement or nutraceutical composition comprising from 0.1 to 99.9% by weight of a S-sulfonated keratin protein fraction nutraceutical agent, and at least one of from 40 to 90% by weight cellulose or derivative thereof, from 15 to 60% by weight starch or derivative thereof, from 15 to 60% by weight starch and derivative thereof, from 2 to 95% sweetener, from 0.1 to 60% Vitamin C or from 2 to 15% sodium sulfite.

2. The oral supplement or nutraceutical composition of claim 1 wherein the S-sulfonated keratin protein fraction nutraceutical agent comprises keratin intermediate filament protein.

3. The oral supplement or nutraceutical composition of claim 2 wherein the S-sulfonated keratin protein fraction nutraceutical agent is intact.

4. The oral supplement or nutraceutical composition of claim 2 wherein the S-sulfonated keratin protein fraction nutraceutical agent is hydrolyzed.

5. The oral supplement or nutraceutical composition of claim 1 wherein the S-sulfonated keratin protein fraction nutraceutical agent comprises High Sulfur Protein (HSP).

6. The oral supplement or nutraceutical composition of claim 5 wherein the S-sulfonated keratin protein fraction nutraceutical agent is intact.

7. The oral supplement or nutraceutical composition of claim 5 wherein the S-sulfonated keratin protein fraction nutraceutical agent is hydrolyzed.

8. A method for preparing an oral supplement or nutraceutical composition comprising formulating a S-sulfonated keratin protein fraction nutraceutical agent with at least one of cellulose or derivative thereof, starch or derivative thereof, sweetener or sodium sulfite.

9. The oral supplement or nutraceutical composition of claim 1 wherein the oral supplement or nutraceutical composition is a mixture of the S-sulfonated keratin protein fraction nutraceutical agent and the at least one of cellulose or derivative thereof, starch or derivative thereof, starch and derivative thereof, sweetener, Vitamin C or sodium sulfite.

10. The oral supplement or nutraceutical composition of claim 1, wherein the S-sulfonated keratin protein fraction nutraceutical agent is intact.

11. The oral supplement or nutraceutical composition of claim 1, wherein the S-sulfonated keratin protein fraction nutraceutical agent is hydrolyzed.

* * * * *